US012176080B2

(12) United States Patent
Vozila et al.

(10) Patent No.: US 12,176,080 B2
(45) Date of Patent: *Dec. 24, 2024

(54) SYSTEM AND METHOD FOR REVIEW OF AUTOMATED CLINICAL DOCUMENTATION FROM RECORDED AUDIO

(71) Applicant: Nuance Communications, Inc., Burlington, MA (US)

(72) Inventors: Paul Joseph Vozila, Arlington, MA (US); Guido Remi Marcel Gallopyn, Newburyport, MA (US); Uwe Helmut Jost, Groton, MA (US); Matthias Helletzgruber, Vienna (AT); Jeremy Martin Jancsary, Vienna (AT); Kumar Abhinav, Montreal (CA); Joel Praveen Pinto, Aachen (DE); Donald E. Owen, Orlando, FL (US); Mehmet Mert Öz, Baden (AT)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,799

(22) Filed: Jan. 10, 2022

(65) Prior Publication Data

US 2022/0130502 A1 Apr. 28, 2022

Related U.S. Application Data

(63) Continuation of application No. 16/292,920, filed on Mar. 5, 2019, now Pat. No. 11,222,716.

(Continued)

(51) Int. Cl.
  *G06F 3/0482* (2013.01)
  *G06F 3/0485* (2022.01)
  (Continued)

(52) U.S. Cl.
  CPC .......... *G16H 10/60* (2018.01); *G06F 3/0482* (2013.01); *G06F 3/0485* (2013.01); *G06F 3/165* (2013.01);
  (Continued)

(58) Field of Classification Search
  None
  See application file for complete search history.

(56) References Cited

U.S. PATENT DOCUMENTS 5,357,427 A 10/1994 Langen et al.
6,004,276 A 12/1999 Wright et al.
(Continued)

FOREIGN PATENT DOCUMENTS

WO 9844484 A1 10/1998
WO 2005093716 A1 10/2005
(Continued)

OTHER PUBLICATIONS

"Non Final Office Action Issued in U.S. Appl. No. 17/846,355", dated Sep. 27, 2023, 16 Pages.
(Continued)

*Primary Examiner* — Ariel Mercado-Vargas
(74) *Attorney, Agent, or Firm* — Brian J. Colandreo; Heath M. Sargeant; Holland & Knight LLP

(57) ABSTRACT

A method, computer program product, and computing system for obtaining, by a computing device, encounter information of a patient encounter, wherein the encounter information may include audio encounter information obtained from at least a first encounter participant. The audio encounter information obtained from at least the first encounter participant may be processed. A user interface may be generated displaying a plurality of layers associated with the audio encounter information obtained from at least the first encounter participant. A user input may be received from a
(Continued)

peripheral device to navigate through each of the plurality of layers associated with the audio encounter information displayed on the user interface.

20 Claims, 15 Drawing Sheets

Related U.S. Application Data

(60) Provisional application No. 62/803,193, filed on Feb. 8, 2019, provisional application No. 62/638,809, filed on Mar. 5, 2018.

(51) Int. Cl.
| | | |
|---|---|---|
| *G06F 3/16* | (2006.01) | |
| *G06F 40/169* | (2020.01) | |
| *G06N 20/00* | (2019.01) | |
| *G10L 15/22* | (2006.01) | |
| *G10L 15/26* | (2006.01) | |
| *G16H 10/20* | (2018.01) | |
| *G16H 10/60* | (2018.01) | |
| *G16H 15/00* | (2018.01) | |
| *G16H 40/60* | (2018.01) | |
| *G06F 3/033* | (2013.01) | |
| *G06F 3/0362* | (2013.01) | |
| *G06F 3/0489* | (2022.01) | |

(52) U.S. Cl.
CPC ............ *G06F 3/167* (2013.01); *G06F 40/169* (2020.01); *G06N 20/00* (2019.01); *G10L 15/22* (2013.01); *G10L 15/26* (2013.01); *G16H 10/20* (2018.01); *G16H 15/00* (2018.01); *G16H 40/60* (2018.01); *G06F 3/0334* (2013.01); *G06F 3/0362* (2013.01); *G06F 3/0489* (2013.01)

(56) References Cited

U.S. PATENT DOCUMENTS

| | | | |
|---|---|---|---|
| 8,132,104 B2 | 3/2012 | Ash et al. | |
| 8,589,379 B2 * | 11/2013 | Hirasawa | G16H 50/70 |
| | | | 704/235 |
| 9,104,985 B2 | 8/2015 | Drucker et al. | |
| 9,479,931 B2 | 10/2016 | Ortiz et al. | |
| 9,509,676 B1 | 11/2016 | Johnson et al. | |
| 9,679,107 B2 | 6/2017 | Cardoza et al. | |
| 10,212,588 B2 | 2/2019 | Grim et al. | |
| 10,354,054 B2 | 7/2019 | Kobres et al. | |
| 10,546,655 B2 | 1/2020 | Owen et al. | |
| 10,650,824 B1 | 5/2020 | Kesharaju et al. | |
| 10,691,783 B2 | 6/2020 | Frempong et al. | |
| 10,701,081 B2 | 6/2020 | Grim et al. | |
| 10,719,222 B2 | 7/2020 | Strader et al. | |
| 10,803,436 B2 | 10/2020 | Kobres et al. | |
| 10,957,427 B2 | 3/2021 | Owen et al. | |
| 10,957,428 B2 | 3/2021 | Owen et al. | |
| 10,972,682 B1 | 4/2021 | Muenster et al. | |
| 10,978,187 B2 | 4/2021 | Owen et al. | |
| 11,043,288 B2 | 6/2021 | Gallopyn et al. | |
| 11,074,996 B2 | 7/2021 | Gallopyn et al. | |
| 11,101,022 B2 | 8/2021 | Owen | |
| 11,101,023 B2 | 8/2021 | Gallopyn et al. | |
| 11,114,186 B2 | 9/2021 | Owen | |
| 11,177,034 B2 | 11/2021 | Lyman et al. | |
| 11,216,480 B2 | 1/2022 | Öz et al. | |
| 11,222,103 B1 | 1/2022 | Gallopyn et al. | |
| 11,227,588 B2 | 1/2022 | Wolff et al. | |
| 11,227,679 B2 | 1/2022 | Owen et al. | |
| 11,238,226 B2 | 2/2022 | Vozila et al. | |
| 11,250,383 B2 | 2/2022 | Sharma et al. | |
| 11,257,576 B2 | 2/2022 | Owen et al. | |
| 11,270,261 B2 | 3/2022 | Vozila | |
| 11,295,838 B2 | 4/2022 | Owen et al. | |
| 11,295,839 B2 | 4/2022 | Owen et al. | |
| 11,316,865 B2 | 4/2022 | Gallopyn et al. | |
| 11,322,231 B2 | 5/2022 | Owen et al. | |
| 11,368,454 B2 | 6/2022 | Whaley et al. | |
| 11,402,976 B1 | 8/2022 | Palamadai et al. | |
| 11,483,707 B2 | 10/2022 | Leblang et al. | |
| 11,538,567 B2 | 12/2022 | Davies | |
| 2001/0044588 A1 | 11/2001 | Mault | |
| 2003/0051214 A1 | 3/2003 | Graham et al. | |
| 2003/0105631 A1 | 6/2003 | Habte | |
| 2005/0154588 A1 * | 7/2005 | Janas, III | G16H 10/60 |
| | | | 704/249 |
| 2006/0061595 A1 | 3/2006 | Goede et al. | |
| 2006/0069545 A1 | 3/2006 | Wu et al. | |
| 2006/0106645 A1 | 5/2006 | Bergelson et al. | |
| 2008/0222734 A1 | 9/2008 | Redlich et al. | |
| 2008/0243544 A1 | 10/2008 | Cafer | |
| 2009/0023555 A1 | 1/2009 | Raymond | |
| 2009/0076855 A1 | 3/2009 | Mccord | |
| 2009/0089082 A1 | 4/2009 | Heckerman et al. | |
| 2009/0132276 A1 | 5/2009 | Petera | |
| 2009/0157385 A1 | 6/2009 | Tian et al. | |
| 2009/0178144 A1 | 7/2009 | Redlich et al. | |
| 2009/0248444 A1 | 10/2009 | Harnick | |
| 2009/0304254 A1 | 12/2009 | Yoshida | |
| 2010/0094650 A1 | 4/2010 | Tran et al. | |
| 2010/0191519 A1 | 7/2010 | Morton et al. | |
| 2011/0254954 A1 | 10/2011 | Lee | |
| 2012/0041949 A1 * | 2/2012 | Hirasawa | G16H 50/70 |
| | | | 707/723 |
| 2012/0081504 A1 | 4/2012 | Ng et al. | |
| 2012/0173269 A1 | 7/2012 | Omidi | |
| 2012/0173278 A1 | 7/2012 | Herbst et al. | |
| 2012/0173281 A1 * | 7/2012 | DiLella | G16H 10/20 |
| | | | 705/3 |
| 2012/0197648 A1 * | 8/2012 | Moloney | G10L 19/018 |
| | | | 381/56 |
| 2012/0209625 A1 | 8/2012 | Armstrong et al. | |
| 2012/0330876 A1 | 12/2012 | Bryce | |
| 2013/0311190 A1 | 11/2013 | Reiner | |
| 2013/0317838 A1 | 11/2013 | Schoenberg | |
| 2013/0325488 A1 | 12/2013 | Carter et al. | |
| 2014/0013219 A1 * | 1/2014 | Liu | G06F 40/56 |
| | | | 715/255 |
| 2014/0047375 A1 | 2/2014 | Koll et al. | |
| 2014/0136973 A1 | 5/2014 | Kumar et al. | |
| 2014/0188516 A1 | 7/2014 | Kamen et al. | |
| 2014/0207491 A1 * | 7/2014 | Zimmerman | G16Z 99/00 |
| | | | 705/3 |
| 2014/0253876 A1 | 9/2014 | Klin | |
| 2014/0275928 A1 | 9/2014 | Acquista et al. | |
| 2014/0278448 A1 | 9/2014 | Sadeghi et al. | |
| 2014/0282008 A1 | 9/2014 | Verard | |
| 2014/0344679 A1 * | 11/2014 | Larsen | G16H 10/60 |
| | | | 715/256 |
| 2014/0358585 A1 | 12/2014 | Reiner | |
| 2015/0106123 A1 | 4/2015 | Amarasingham | |
| 2015/0149207 A1 | 5/2015 | O'keefe | |
| 2015/0154358 A1 | 6/2015 | Anderson et al. | |
| 2015/0182296 A1 | 7/2015 | Daon | |
| 2015/0220637 A1 * | 8/2015 | Goetz | H04N 21/251 |
| | | | 348/468 |
| 2016/0063191 A1 | 3/2016 | Vesto et al. | |
| 2016/0110350 A1 | 4/2016 | Waibel | |
| 2016/0210429 A1 | 7/2016 | Ortiz et al. | |
| 2016/0239617 A1 | 8/2016 | Farooq et al. | |
| 2016/0364526 A1 | 12/2016 | Reicher et al. | |
| 2016/0366299 A1 | 12/2016 | Sato | |
| 2017/0006135 A1 | 1/2017 | Siebel et al. | |
| 2017/0039502 A1 | 2/2017 | Guman | |
| 2017/0098051 A1 | 4/2017 | Balram | |
| 2017/0185716 A1 | 6/2017 | Rodriguez et al. | |
| 2017/0186441 A1 | 6/2017 | Wenus | |
| 2017/0277993 A1 | 9/2017 | Beaver | |
| 2017/0287031 A1 | 10/2017 | Barday | |
| 2017/0295075 A1 | 10/2017 | Roebuck | |

(56) References Cited

U.S. PATENT DOCUMENTS

| | | |
|---|---|---|
| 2017/0300648 A1 | 10/2017 | Charlap |
| 2018/0167243 A1 | 6/2018 | Gerdes |
| 2019/0051374 A1 | 2/2019 | Vozila et al. |
| 2019/0051375 A1 | 2/2019 | Owen et al. |
| 2019/0051376 A1 | 2/2019 | Gallopyn et al. |
| 2019/0051379 A1 | 2/2019 | Owen et al. |
| 2019/0051380 A1 | 2/2019 | Owen et al. |
| 2019/0051394 A1 | 2/2019 | Owen et al. |
| 2019/0066823 A1 | 2/2019 | Owen |
| 2019/0121532 A1* | 4/2019 | Strader ................. G06F 40/289 |
| 2019/0272147 A1 | 9/2019 | Vozila et al. |
| 2019/0272895 A1 | 9/2019 | Vozila et al. |
| 2019/0272897 A1 | 9/2019 | Öz et al. |
| 2019/0272899 A1 | 9/2019 | Drexel et al. |
| 2019/0272900 A1 | 9/2019 | Jancsary et al. |
| 2019/0272901 A1 | 9/2019 | Almendro Barreda et al. |
| 2019/0272902 A1 | 9/2019 | Vozila et al. |
| 2019/0272906 A1 | 9/2019 | Vozila et al. |
| 2020/0005949 A1 | 1/2020 | Warkentine |
| 2020/0160951 A1 | 5/2020 | Owen et al. |
| 2020/0342966 A1 | 10/2020 | Stern |
| 2021/0099433 A1 | 4/2021 | Soryal et al. |
| 2021/0210180 A1 | 7/2021 | Owen et al. |
| 2021/0210181 A1 | 7/2021 | Owen et al. |
| 2021/0210200 A1 | 7/2021 | Gallopyn et al. |
| 2021/0233634 A1 | 7/2021 | Owen et al. |
| 2021/0233652 A1 | 7/2021 | Owen et al. |
| 2021/0243412 A1 | 8/2021 | Owen et al. |
| 2021/0407635 A1 | 12/2021 | Owen |
| 2022/0051772 A1 | 2/2022 | Gallopyn et al. |
| 2022/0180318 A1 | 6/2022 | Barreda et al. |
| 2022/0208322 A1 | 6/2022 | Owen et al. |
| 2022/0210161 A1 | 6/2022 | Gallopyn et al. |
| 2022/0319653 A1 | 10/2022 | Owen et al. |
| 2023/0014971 A1 | 1/2023 | Drexel et al. |
| 2023/0021529 A1 | 1/2023 | Bhattacherjee et al. |
| 2023/0092558 A1 | 3/2023 | Vozila et al. |
| 2023/0290023 A1 | 9/2023 | Tsunomori et al. |

FOREIGN PATENT DOCUMENTS

| | | |
|---|---|---|
| WO | 2013118510 A1 | 8/2013 |
| WO | 2015021208 A1 | 2/2015 |
| WO | 2016149794 A1 | 9/2016 |
| WO | 2017100334 A1 | 6/2017 |
| WO | 2018132336 A1 | 7/2018 |

OTHER PUBLICATIONS

"Non Final Office Action Issued in U.S. Appl. No. 17/210,233", dated Oct. 23, 2023, 47 Pages.

"Non Final Office Action Issued in U.S. Appl. No. 17/678,791", dated Nov. 9, 2023, 8 Pages.

"Non Final Office Action Issued in U.S. Appl. No. 17/955,693", dated Nov. 9, 2023, 8 Pages.

Sapru, et al., "Improving Speaker Diarization using Social Role Information", In Proceedings of International Conference on Acoustics, Speech and Signal Processing, May 4, 2014, pp. 101-105.

Shen, et al., "Auto-encoding twin-bottleneck hashing", In Proceedings of the IEEE/CVF Conference on Computer Vision and Pattern Recognition, Jun. 13, 2020, pp. 2818-2827.

"Notice of Allowance Issued in U.S. Appl. No. 17/467,688", dated Oct. 6, 2022, 9 Pages.

"Non Final Office Action Issued in U.S. Appl. No. 17/696,165", dated Nov. 25, 2022, 7 Pages.

"Office Action Issued in European Patent Application No. 18844675.1", dated Mar. 4, 2022, 6 Pages.

"Extended European Search Report Issued in European Application No. 18844829.4", dated Apr. 30, 2021, 9 Pages.

"Extended European Search Report Issued in Application No. 19763338.1", dated Apr. 4, 2022, 8 Pages.

"European Extended Search Report for Application No. 19763474.4", dated Apr. 8, 2022, 8 Pages.

"Extended European Search Report Issued in Application No. 19763475.1", dated Apr. 12, 2022, 10 Pages.

"Search Report Issued in European Patent Application No. 19763477.7", dated Mar. 28, 2022, 10 Pages.

"Search Report Issued in European Patent Application No. 19763600.4", dated Mar. 31, 2022, 9 Pages.

"Search Report Issued in European Patent Application No. 19763678.0", dated Mar. 25, 2022, 8 Pages.

"Search Report Issued in European Patent Application No. 19763834.9", dated Dec. 10, 2021, 9 Pages.

"Search Report Issued in European Patent Application No. 19764329.9", dated Dec. 14, 2021, 13 Pages.

Hoof, et al., "Ageing-in-place with the use of ambient intelligence technology: Perspectives of older users", In International Journal of Medical Informatics, vol. 80, Issue 5, May 1, 2011, pp. 310-331.

"International Search Report and Written Opinion Issued in PCT Application No. PCT/US21/056274", dated Dec. 7, 2021, 7 Pages.

"International Search Report and Written Opinion Issued in PCT Application No. PCT/US22/021375", dated Jul. 26, 2022, 8 Pages.

"International Search Report and Written Opinion Issued in PCT Application No. PCT/US22/021393", dated Sep. 2, 2022, 12 Pages.

"Invitation To Pay Additional Fees Issued in PCT Application No. PCT/US22/021393", dated Jun. 24, 2022, 2 Pages.

"International Search Report and Written Opinion Issued in PCT Application No. PCT/US22/021412", dated Sep. 2, 2022, 11 Pages.

"Invitation To Pay Additional Fees Issued in PCT Application No. PCT/US22/021412", dated Jun. 24, 2022, 2 Pages.

"International Search Report and Written Opinion Issued in PCT Application No. PCT/US22/021419", dated Sep. 23, 2022, 13 Pages.

"Invitation To Pay Additional Fees Issued in PCT Application No. PCT/US22/021419", dated Jul. 5, 2022, 2 Pages.

"International Search Report and Written Opinion Issued in PCT Application No. PCT/US22/021422", dated Sep. 2, 2022, 11 Pages.

"Invitation To Pay Additional Fees Issued in PCT Application No. PCT/US22/021422", dated Jun. 24, 2022, 2 Pages.

Pusateri, et al., "A Mostly Data-Driven Approach to Inverse Text Normalization", In Proceedings of Interspeech, Aug. 20, 2017, pp. 2784-2788.

"Notice of Allowance Issued in U.S. Appl. No. 16/058,914", dated Jan. 5, 2023, 11 Pages.

"Non Final Office Action Issued in U.S. Appl. No. 17/991,234", dated Mar. 14, 2023, 42 Pages.

Watanabe, et al., "Hybrid CTC/Attention Architecture for End-to-End Speech Recognition", In Journal of IEEE Selected Topics in Signal Processing, vol. 11, Issue 8, Dec. 2017, pp. 1240-1253.

Shivappa, et al., "Person Tracking With Audio-visual Cues Using The Iterative Decoding Framework", In Proceedings of the IEEE Fifth International Conference on Advanced Video and Signal Based Surveillance, Sep. 1, 2008, pp. 260-267.

"Office Action Issued in European Patent Application No. 18843329.6", dated Feb. 24, 2023, 5 Pages.

"Notice of Allowance Issued in U.S. Appl. No. 17/210,052", dated Jan. 30, 2023, 5 Pages.

"Final Office Action Issued in U.S. Appl. No. 16/292,895", dated Jan. 5, 2023, 17 Pages.

"Final Office Action Issued in U.S. Appl. No. 16/058,803", dated Mar. 20, 2023, 12 Pages.

"Notice of Allowance Issued in U.S. Appl. No. 17/210,052", dated Apr. 10, 2023, 5 Pages.

"Notice of Allowance Issued in U.S. Appl. No. 17/696,165", dated Apr. 26, 2023, 7 Pages.

"Notice of Allowance Issued in European Patent Application No. 18843586.1", dated Mar. 14, 2023, 8 Pages.

"Notice of Allowance Issued In European Patent Application No. 18843586.1", dated Jun. 9, 2023, 2 Pages.

"Final Office Action Issued in U.S. Appl. No. 17/991,234", dated Jul. 11, 2023, 35 Pages.

"Final Office Action Issued in U.S. Appl. No. 16/058,803", dated May 18, 2022, 12 Pages.

(56) References Cited

OTHER PUBLICATIONS

"Non Final Office Action Issued in U.S. Appl. No. 16/058,803", dated Sep. 21, 2022, 11 Pages.
"Final Office Action Issued in U.S. Appl. No. 16/058,826", dated Aug. 19, 2022, 37 Pages.
"Non Final Office Action Issued in U.S. Appl. No. 16/058,826", dated Mar. 29, 2022, 37 Pages.
"Notice of Allowance Issued in U.S. Appl. No. 16/058,829", dated Jun. 3, 2022, 9 Pages.
"Notice of Allowance Issued in U.S. Appl. No. 16/058,883", dated Jun. 2, 2022, 2 Pages.
"Notice of Allowance Issued in U.S. Appl. No. 16/058,883", dated Mar. 25, 2022, 9 Pages.
"Final Office Action Issued in U.S. Appl. No. 16/058,894", dated Aug. 17, 2022, 45 Pages.
"Non Final Office Action Issued in U.S. Appl. No. 16/058,894", dated Mar. 31, 2022, 44 Pages.
"Non Final Office Action Issued in U.S. Appl. No. 16/058,914", dated May 24, 2022, 9 Pages.
"Notice of Allowance Issued in U.S. Appl. No. 16/058,914", dated Sep. 14, 2022, 11 Pages.
"Notice of Allowance Issued in U.S. Appl. No. 16/058,914", dated Mar. 30, 2022, 12 Pages.
"Final Office Action Issued in U.S. Appl. No. 16/058,925", dated Oct. 20, 2022, 23 Pages.
"Non Final Office Action Issued in U.S. Appl. No. 16/058,925", dated Mar. 30, 2022, 21 Pages.
"Advisory Action Issued in U.S. Appl. No. 16/058,936", dated Aug. 19, 2020, 5 Pages.
"Notice of Allowance Issued in U.S. Appl. No. 16/058,951", dated Nov. 15, 2019, 11 Pages.
"Final Office Action Issued in U.S. Appl. No. 16/059,818", dated Apr. 7, 2020, 7 Pages.
"Advisory Action Issued In U.S. Appl. No. 16/059,895", dated Sep. 10, 2020, 5 Pages.
"Notice of Allowance Issued in U.S. Appl. No. 16/059,895", dated Jan. 18, 2022, 10 Pages.
"Final Office Action Issued in U.S. Appl. No. 16/059,967", dated Apr. 1, 2022, 10 Pages.
"Advisory Action Issued In U.S. Appl. No. 16/059,974", dated Sep. 15, 2020, 5 Pages.
"Non Final Office Action Issued in U.S. Appl. No. 16/059,974", dated Dec. 18, 2020, 20 Pages.
"Notice of Allowance Issued in U.S. Appl. No. 16/059,974", dated Feb. 4, 2022, 11 Pages.
"Advisory Action Issued In U.S. Appl. No. 16/059,986", dated Sep. 15, 2020, 5 Pages.
"Final Office Action issued in related U.S. Appl. No. 16/100,030", dated May 8, 2020, 10 Pages.
"Notice of Allowance Issued in U.S. Appl. No. 16/270,782", dated Dec. 16, 2021, 9 Pages.
"Non Final Office Action Issued in U.S. Appl. No. 16/270,888", dated Jan. 20, 2022, 10 Pages.
"Notice of Allowance Issued in U.S. Appl. No. 16/270,888", dated Jul. 13, 2022, 8 Pages.
"Non Final Office Action Issued in U.S. Appl. No. 16/271,029", dated Jun. 21, 2022, 30 Pages.
"Final Office Action Issued in U.S. Appl. No. 16/271,029", dated Jan. 31, 2022, 39 Pages.
"Final Office Action Issued in U.S. Appl. No. 16/292,877", dated Nov. 14, 2022, 10 Pages.
"Final Office Action Issued in U.S. Appl. No. 16/292,877", dated Feb. 8, 2021, 11 Pages.
"Non Final Office Action Issued in U.S. Appl. No. 16/292,877", dated May 2, 2022, 10 Pages.
"Final Office Action Issued in U.S. Appl. No. 16/292,893", dated Jul. 28, 2022, 39 Pages.
"Non Final Office Action Issued in U.S. Appl. No. 16/292,893", dated Mar. 29, 2022, 37 Pages.
"Non Final Office Action Issued in U.S. Appl. No. 16/292,895", dated May 17, 2022, 17 Pages.
"Final Office Action Issued in U.S. Appl. No. 16/292,973", dated Oct. 28, 2022, 27 Pages.
"Non Final Office Action Issued in U.S. Appl. No. 16/292,973", dated Apr. 1, 2022, 26 Pages.
"Non Final Office Action Issued in U.S. Appl. No. 16/293,032", dated Apr. 5, 2022, 37 Pages.
"Notice of Allowance Issued in U.S. Appl. No. 16/293,032", dated Jul. 25, 2022, 11 Pages.
"Non Final Office Action Issued in U.S. Appl. No. 16/588,475", dated Jan. 10, 2022, 17 Pages.
"Non Final Office Action Issued in U.S. Appl. No. 16/588,475", dated Sep. 16, 2022, 17 Pages.
"Non Final Office Action Issued in U.S. Appl. No. 16/588,897", dated Mar. 31, 2022, 6 Pages.
"Notice of Allowance Issued in U.S. Appl. No. 16/588,897", dated Sep. 2, 2022, 8 Pages.
"Notice of Allowance Issued in U.S. Appl. No. 17/084,448", dated Jan. 26, 2022, 5 Pages.
"Notice of Allowance Issued in U.S. Appl. No. 17/210,052", dated Feb. 18, 2022, 7 Pages.
"Notice of Allowance Issued in U.S. Appl. No. 17/210,052", dated Sep. 9, 2022, 8 Pages.
"Non Final Office Action Issued in U.S. Appl. No. 17/210,120", dated Nov. 1, 2021, 14 Pages.
"Notice of Allowance Issued in U.S. Appl. No. 17/210,120", dated Jun. 10, 2022, 7 Pages.
"Notice of Allowance Issued in U.S. Appl. No. 17/210,120", dated Mar. 1, 2022, 8 Pages.
Notice of Allowance mailed on Jan. 31, 2024, in U.S. Appl. No. 17/846,355, 8 Pages.
Non-Final Office Action mailed on Dec. 11, 2023, in U.S. Appl. No. 17/697,593, 23 Pages.
Final Office Action mailed on Mar. 7, 2024, in U.S. Appl. No. 17/210,233, 54 pages.
Communication 94(3) Received for European Application No. 18844406.1, mailed on Apr. 4, 2024, 11 pages.
Communication 94(3) Received for European Application No. 18844669.4, mailed on Apr. 3, 2024, 5 pages.
Communication 94(3) Received for European Application No. 18844829.4, mailed on Apr. 4, 2024, 5 pages.
Communication pursuant to Article 94(3) EPC Received for European Application No. 18843254.6, mailed on Mar. 26, 2024, 08 pages.
Communication pursuant to Article 94(3) EPC Received for European Application No. 18843255.3, mailed on Feb. 26, 2024, 6 pages.
Communication pursuant to Article 94(3) EPC, Received for European Application No. 18843175.3, mailed on Feb. 29, 2024, 09 pages.
Communication pursuant to Article 94(3) EPC, Received for European Application No. 18843945.9, mailed on Mar. 4, 2024, 09 pages.
Communication Pursuant to Article 94(3) EPC, Received for European Application No. 18844407.9, mailed on Feb. 14, 2024, 06 pages.
Communication pursuant to Article 94(3) received in European Application No. 18844530.8, mailed on Apr. 3, 2024, 5 pages.
Communication pursuant to Article 94(3) Received in European Patent Application No. 18844226.3, mailed on Mar. 22, 2024, 7 pages.
Communication under Rule 71(3) EPC Received for European Application No. 18845046.4, mailed on Feb. 29, 2024, 5 pages.
Non-Final Office Action mailed on Apr. 16, 2024, in U.S. Appl. No. 17/210,300, 13 pages.
Notice of Allowance mailed on Apr. 3, 2024, in U.S. Appl. No. 17/678,791, 8 pages.
Weibel, et al., "LAB-IN-A-BOX: semi-automatic tracking of activity in the medical office," Personal Ubiquitous Computing, Springer, Sep. 28, 2014, pp. 317-334.

(56) References Cited

OTHER PUBLICATIONS

Communication pursuant to Article 94(3) EPC, Received for European Application No. 18843648.9, mailed on May 2, 2024, 10 pages.
Communication pursuant to Article 94(3) received in European Application No. 18843873.3, mailed on Apr. 11, 2024, 5 pages.
Communication pursuant to Article 94(3) Received in European Patent Application No. 18845144.7, mailed on May 3, 2024, 10 pages.
Communication pursuant to Article 94(3) EPC Received for European Application No. 18844752.8, mailed on Feb. 7, 2024, 06 pages.
Communication pursuant to Rules 70(2) and 70a(2) Received for European Application No. 1976338.1, mailed on Apr. 25, 2022, 01 pages.
Communication pursuant to Rules 70(2) and 70a(2) Received for European Application No. 19763834.9, mailed on Jan. 5, 2022, 01 pages.
Communication pursuant to Rules 70(2) and 70a(2) Received for European Application No. 19764329.9, mailed on Jan. 12, 2022, 01 pages.
Communication under Rule 71(3) EPC Received for European Application No. 18843874.1, mailed on May 10, 2024, 09 pages.
Final Office Action mailed on Jun. 21, 2024, in U.S. Appl. No. 17/697,593, 28 pages.
Lee, et al., "Portable meeting recorder.", Proceedings of the tenth ACM international conference on Multimedia, 2002, 10 Pages.
Non-Final Office Action mailed on Nov. 2, 2018, in U.S. Appl. No. 16/059,818, 13 pages.
Notice of Allowance mailed on Apr. 4, 2022, in U.S. Appl. No. 17/084,448, 04 pages.
Notice of Allowance mailed on Apr. 17, 2024, in U.S. Appl. No. 17/955,693, 08 pages.
Notice of Allowance mailed on Aug. 10, 2021, in U.S. Appl. No. 16/271,329, 9 pages.
Notice of Allowance mailed on Jan. 27, 2022, in U.S. Appl. No. 16/773,447, 2 pages.
Final Office Action mailed on Aug. 21, 2024, in U.S. Appl. No. 17/210,300, 08 pages.
Non-Final Office Action mailed on Aug. 28, 2024, in U.S. Appl. No. 17/210,292, 20 pages.

* cited by examiner

SYSTEM AND METHOD FOR REVIEW OF AUTOMATED CLINICAL DOCUMENTATION FROM RECORDED AUDIO

RELATED APPLICATION(S)

This application is a continuation of U.S. patent application Ser. No. 16/292,920 filed Mar. 5, 2019, now U.S. Pat. No. 11,222,716, which claims the benefit of the following U.S. Provisional Application Nos. 62/803,193 filed on 8 Feb. 2019 and 62/638,809 filed on 5 Mar. 2018, the contents of which are all incorporated herein by reference.

BACKGROUND

Automated Clinical Documentation (ACD) may be used, e.g., to turn transcribed conversational (e.g., physician, patient, and/or other participants such as patient's family members, nurses, physician assistants, etc.) speech into formatted (e.g., medical) reports. Such reports may be reviewed, e.g., to assure accuracy of the reports by the physician, scribe, etc.

SUMMARY OF DISCLOSURE

In one implementation, a computer-implemented method executed by a computer may include but is not limited to obtaining, by a computing device, encounter information of a patient encounter, wherein the encounter information may include audio encounter information obtained from at least a first encounter participant. The audio encounter information obtained from at least the first encounter participant may be processed. A user interface may be generated displaying a plurality of layers associated with the audio encounter information obtained from at least the first encounter participant. A user input may be received from a peripheral device to navigate through each of the plurality of layers associated with the audio encounter information displayed on the user interface.

One or more of the following features may be included. Processing the first audio encounter information may include defining linkages between each of the plurality of layers associated with the audio encounter information. Receiving the user input may include receiving, via the user input from the peripheral device, a selection of a first portion of the audio encounter information at a first layer of the plurality of layers on the user interface, and an annotation may be displayed of at least one of a second layer of the plurality of layers and a third layer of the plurality of layers corresponding to the first portion of the audio encounter information of the first layer of the plurality of layers selected on the user interface. Receiving the user input may include receiving, via the user input from the peripheral device, a selection of the first portion of the audio encounter information at one of the second layer of the plurality of layers and the third layer of the plurality of layers on the user interface, and audio may be provided of the first layer corresponding to the first portion of the audio encounter information of one of the second layer of the plurality of layers and the third layer of the plurality of layers selected on the user interface. The first layer of the plurality of layers may be an audio signal associated with the audio encounter information, wherein the second layer of the plurality of layers may be a transcript associated with the audio encounter information, and wherein the third layer of the plurality of layers may be a medical report associated with the audio encounter information. The peripheral device may include at least one of a keyboard, a pointing device, a foot pedal, and a dial, and the user input from the peripheral device may include at least one of a keyboard shortcut when the peripheral device is the keyboard, a pointing device action when the peripheral device is the pointing device, raising and lowering of the foot pedal when the peripheral device is the foot pedal, and at least one of a rotating action, an up action, a down action, a left action, a right action, and a pressing action of the dial when the peripheral device is the dial. The user input from the peripheral device may cause the user interface to at least one of switch between sentences in an output of the medical report, switch between sections in the output of the medical report, switch between the medical report and the transcript, one of providing audio of the audio signal and ceasing audio of the audio signal, and one of speeding up the audio of the audio signal and slowing down the audio of the audio signal.

In another implementation, a computer program product resides on a computer readable medium and has a plurality of instructions stored on it. When executed by a processor, the instructions cause the processor to perform operations including but not limited to obtaining, by a computing device, encounter information of a patient encounter, wherein the encounter information may include audio encounter information obtained from at least a first encounter participant. The audio encounter information obtained from at least the first encounter participant may be processed. A user interface may be generated displaying a plurality of layers associated with the audio encounter information obtained from at least the first encounter participant. A user input may be received from a peripheral device to navigate through each of the plurality of layers associated with the audio encounter information displayed on the user interface.

One or more of the following features may be included. Processing the first audio encounter information may include defining linkages between each of the plurality of layers associated with the audio encounter information. Receiving the user input may include receiving, via the user input from the peripheral device, a selection of a first portion of the audio encounter information at a first layer of the plurality of layers on the user interface, and an annotation may be displayed of at least one of a second layer of the plurality of layers and a third layer of the plurality of layers corresponding to the first portion of the audio encounter information of the first layer of the plurality of layers selected on the user interface. Receiving the user input may include receiving, via the user input from the peripheral device, a selection of the first portion of the audio encounter information at one of the second layer of the plurality of layers and the third layer of the plurality of layers on the user interface, and audio may be provided of the first layer corresponding to the first portion of the audio encounter information of one of the second layer of the plurality of layers and the third layer of the plurality of layers selected on the user interface. The first layer of the plurality of layers may be an audio signal associated with the audio encounter information, wherein the second layer of the plurality of layers may be a transcript associated with the audio encounter information, and wherein the third layer of the plurality of layers may be a medical report associated with the audio encounter information. The peripheral device may include at least one of a keyboard, a pointing device, a foot pedal, and a dial, and the user input from the peripheral device may include at least one of a keyboard shortcut when the peripheral device is the keyboard, a pointing device action when the peripheral device is the pointing device, raising and lowering of the foot pedal when the peripheral device is the foot pedal, and at least one of a rotating action, an up action, a down action, a left action, a right action, and a pressing action of the dial when the peripheral device is the dial. The user input from the peripheral device may cause the user interface to at least one of switch between sentences in an output of the medical report, switch between sections in the output of the medical report, switch between the medical report and the transcript, one of providing audio of the audio signal and ceasing audio of the audio signal, and one of speeding up the audio of the audio signal and slowing down the audio of the audio signal.

In another implementation, a computing system includes a processor and memory is configured to perform operations including but not limited to obtaining, by a computing device, encounter information of a patient encounter, wherein the encounter information may include audio encounter information obtained from at least a first encounter participant. The audio encounter information obtained from at least the first encounter participant may be processed. A user interface may be generated displaying a plurality of layers associated with the audio encounter information obtained from at least the first encounter participant. A user input may be received from a peripheral device to navigate through each of the plurality of layers associated with the audio encounter information displayed on the user interface.

One or more of the following features may be included. Processing the first audio encounter information may include defining linkages between each of the plurality of layers associated with the audio encounter information. Receiving the user input may include receiving, via the user input from the peripheral device, a selection of a first portion of the audio encounter information at a first layer of the plurality of layers on the user interface, and an annotation may be displayed of at least one of a second layer of the plurality of layers and a third layer of the plurality of layers corresponding to the first portion of the audio encounter information of the first layer of the plurality of layers selected on the user interface. Receiving the user input may include receiving, via the user input from the peripheral device, a selection of the first portion of the audio encounter information at one of the second layer of the plurality of layers and the third layer of the plurality of layers on the user interface, and audio may be provided of the first layer corresponding to the first portion of the audio encounter information of one of the second layer of the plurality of layers and the third layer of the plurality of layers selected on the user interface. The first layer of the plurality of layers may be an audio signal associated with the audio encounter information, wherein the second layer of the plurality of layers may be a transcript associated with the audio encounter information, and wherein the third layer of the plurality of layers may be a medical report associated with the audio encounter information. The peripheral device may include at least one of a keyboard, a pointing device, a foot pedal, and a dial, and the user input from the peripheral device may include at least one of a keyboard shortcut when the peripheral device is the keyboard, a pointing device action when the peripheral device is the pointing device, raising and lowering of the foot pedal when the peripheral device is the foot pedal, and at least one of a rotating action, an up action, a down action, a left action, a right action, and a pressing action of the dial when the peripheral device is the dial. The user input from the peripheral device may cause the user interface to at least one of switch between sentences in an output of the medical report, switch between sections in the output of the medical report, switch between the medical report and the transcript, one of providing audio of the audio signal and ceasing audio of the audio signal, and one of speeding up the audio of the audio signal and slowing down the audio of the audio signal.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
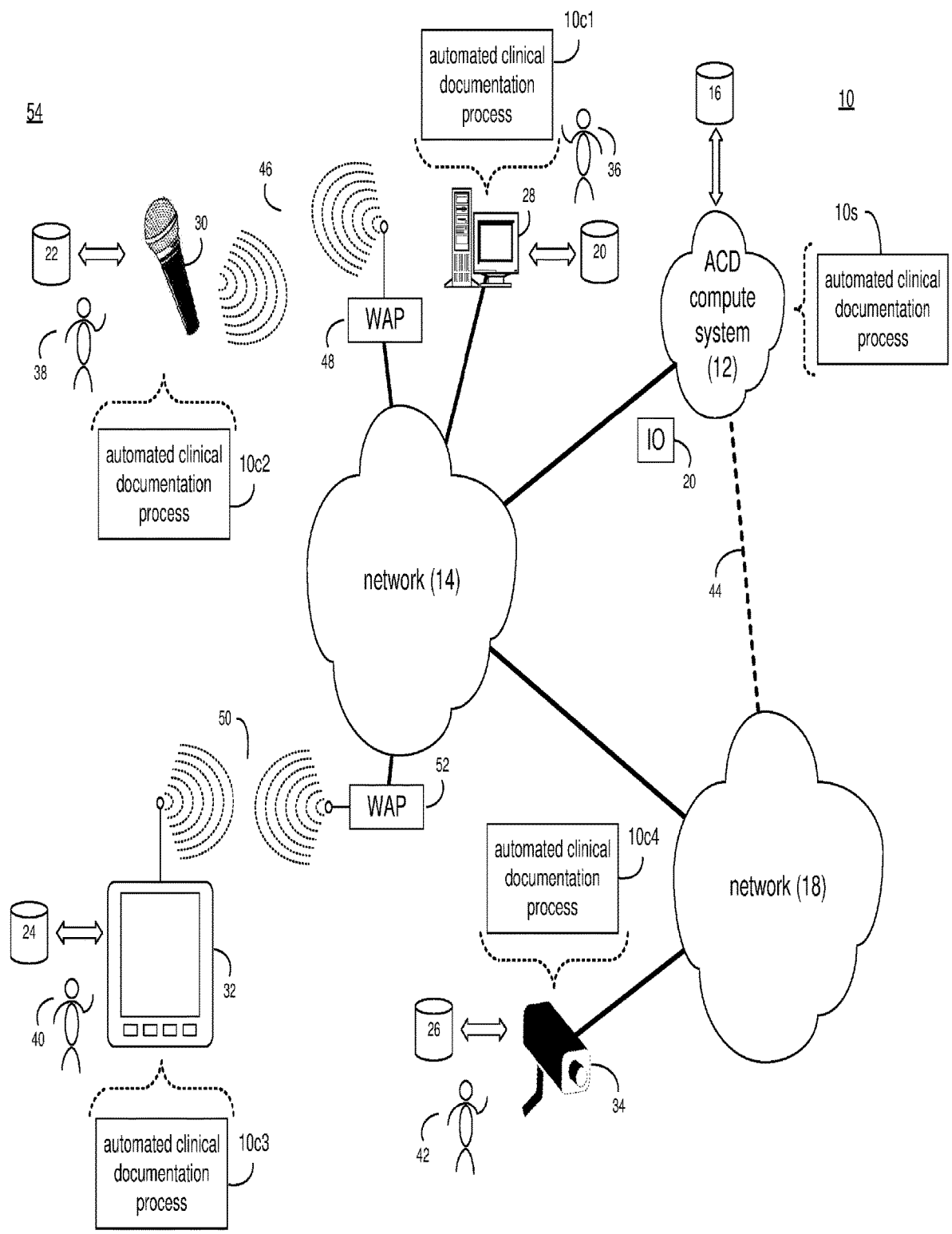
FIG. 1 is a diagrammatic view of an automated clinical documentation computer system and an automated clinical documentation process coupled to a distributed computing network.

System Overview:

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10*s*. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) computer system 12, which may be connected to network 14 (e.g., the Internet or a local area network). ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD computer system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD computer system 12, may be executed by one or more processors (not shown) and one or more memory architectures (not shown) included within ACD computer system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated clinical documentation process 10s, automated clinical documentation process 10c1, automated clinical documentation process 10c2, automated clinical documentation process 10c3 and/or automated clinical documentation process 10c4 to ACD computer system 12. Examples of IO request 20 may include but are not limited to data write requests (i.e. a request that content be written to ACD computer system 12) and data read requests (i.e. a request that content be read from ACD computer system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD computer system 12 directly through network 14 or through secondary network 18. Further, ACD computer system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD computer system 12 may form modular ACD system 54.

Figure 2:
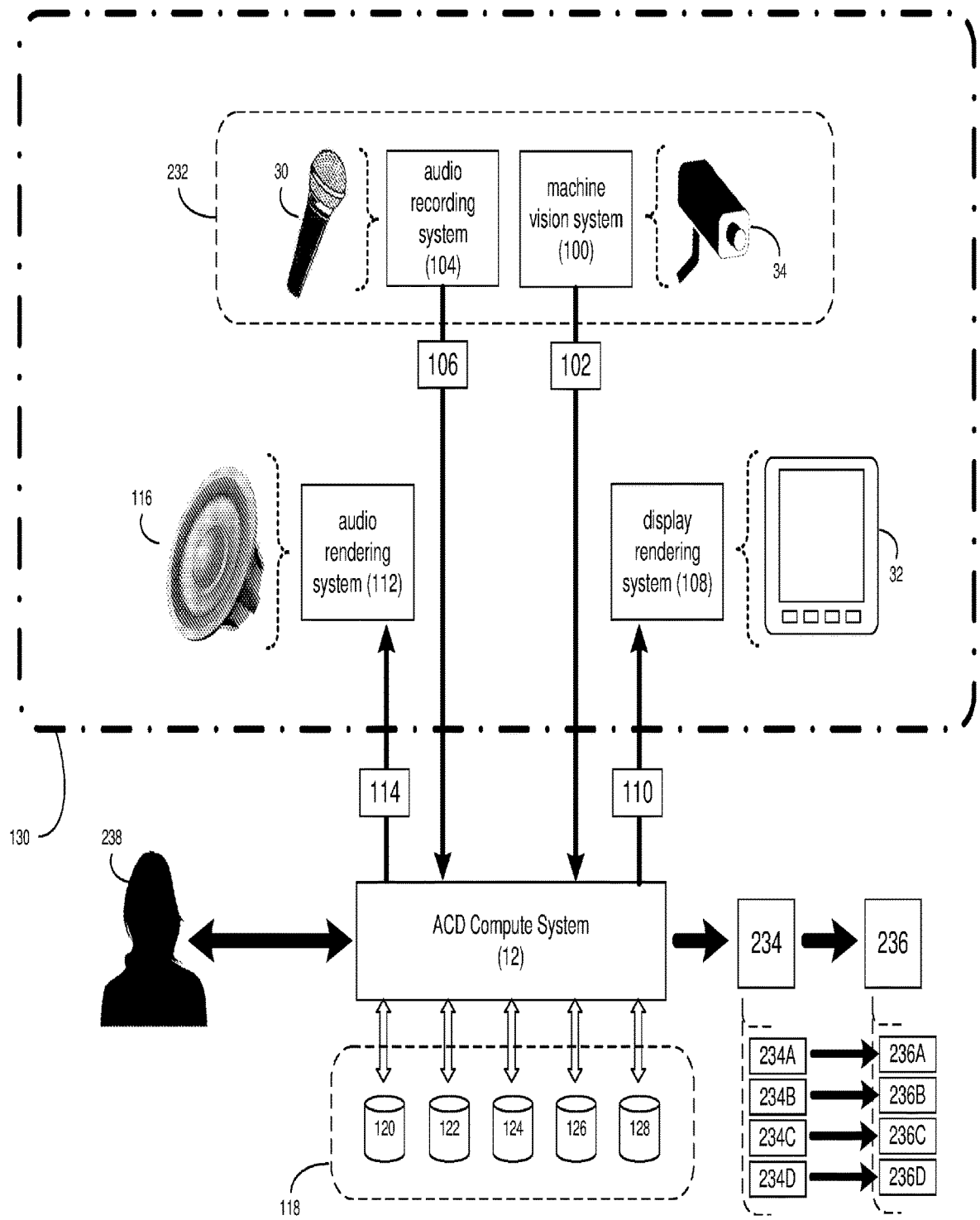
FIG. 2 is a diagrammatic view of a modular ACD system incorporating the automated clinical documentation computer system of FIG. 1.

Referring also to FIG. 2, there is shown a simplified example embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a computer system (e.g., ACD computer system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD computer system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD computer system 12 may include a plurality of discrete computer systems. As discussed above, ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD computer system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
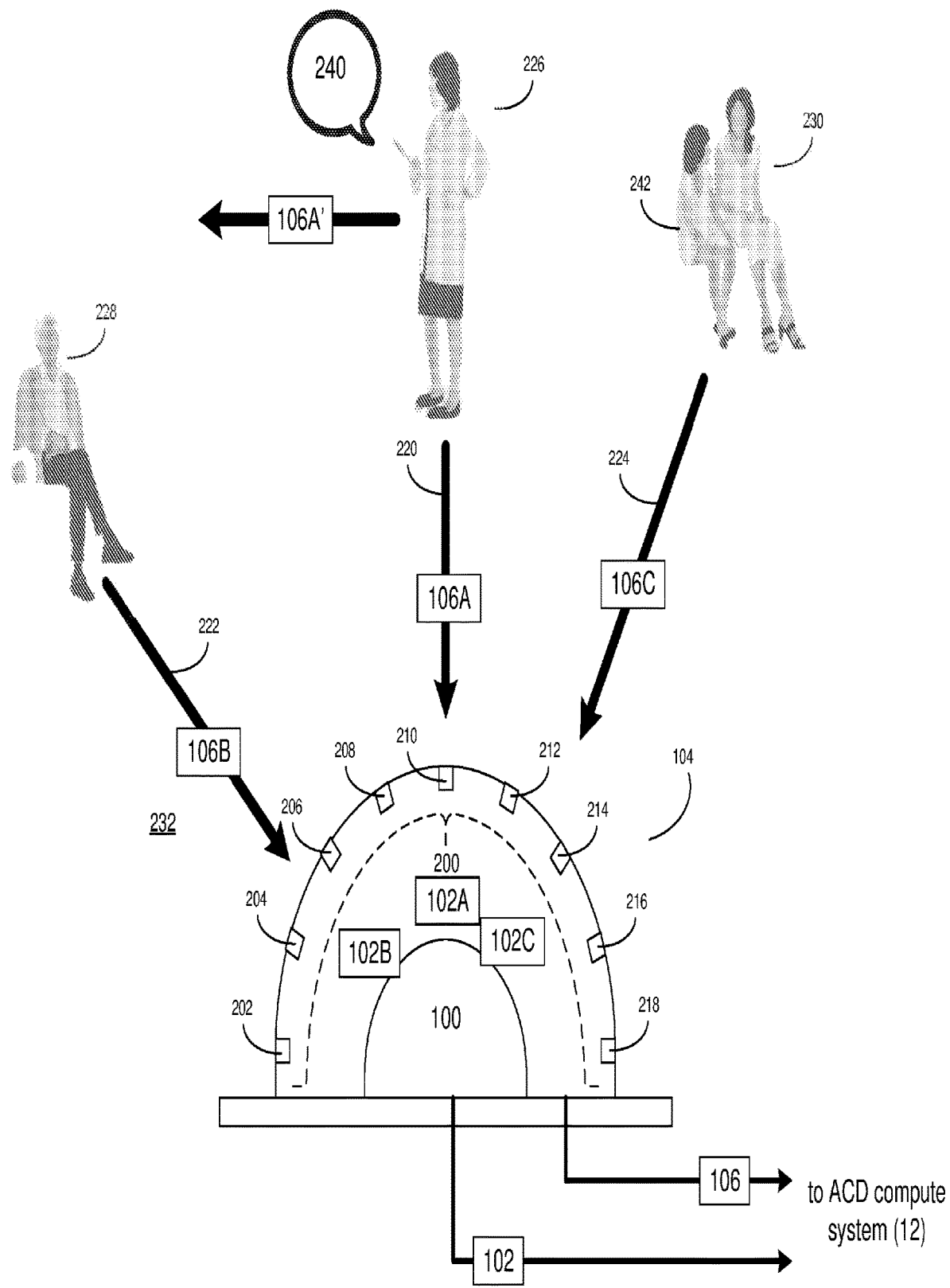
FIG. 3 is a diagrammatic view of a mixed-media ACD device included within the modular ACD system of FIG. 2.
Figure 4:
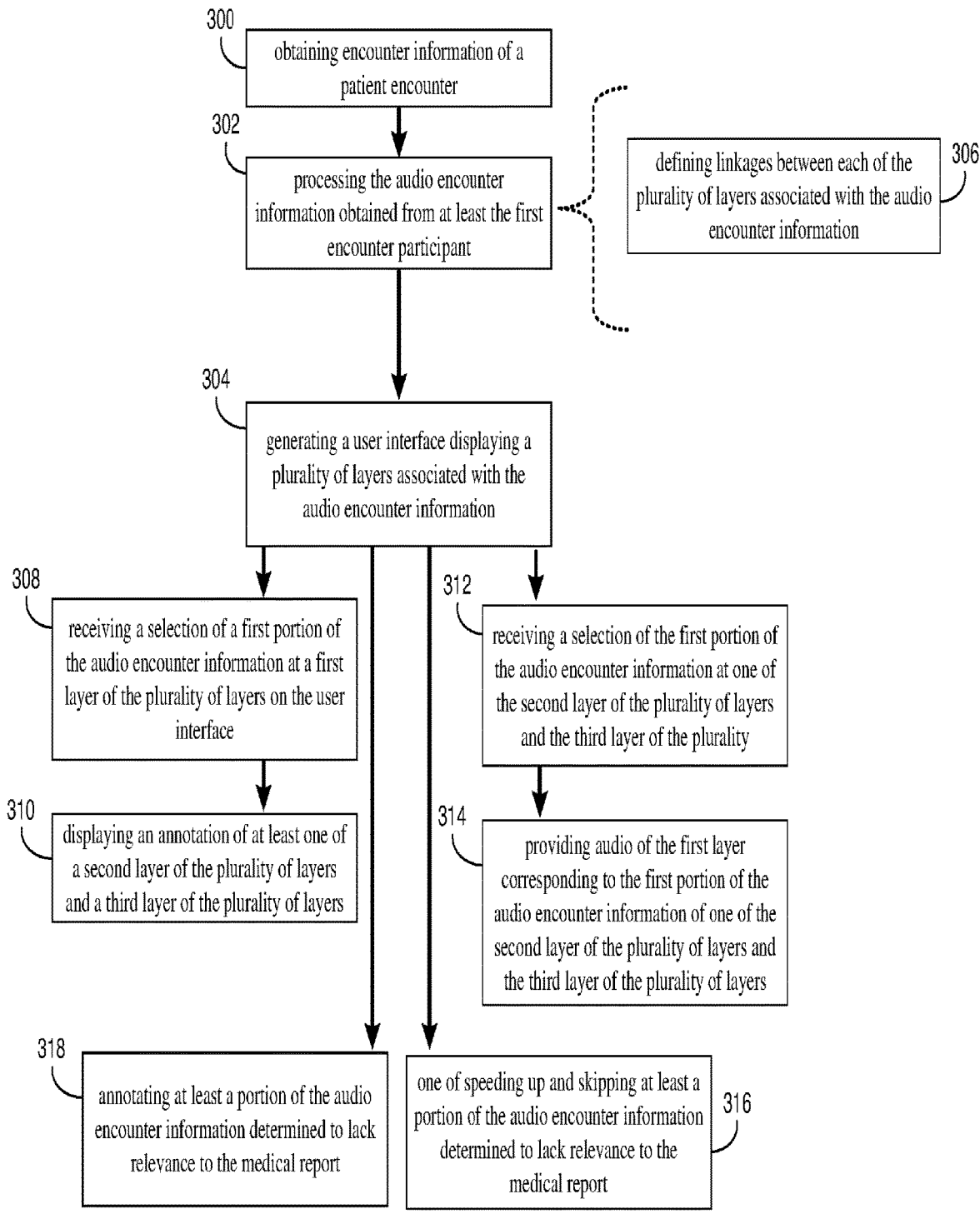
FIG. 4 is a flow chart of one implementation of the automated clinical documentation process of FIG. 1.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD computer system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD computer system 12 may be included within mixed-media ACD device 232 or external to mixed-media ACD device 232.

As discussed above, ACD computer system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD computer system 12 and/or one or more of ACD client electronic devices 28, 30, 32, 34.

As discussed above, automated clinical documentation (ACD) process 10 may be configured to automate the collection and processing of clinical encounter information to generate/store/distribute medical records. Accordingly and referring also to FIGS. 4-8, ACD process 10 may be configured to obtain 300 encounter information (e.g., machine vision encounter information 102 and/or audio encounter information 106) of a patient encounter (e.g., a visit to a doctor's office) of at least a first encounter participant, wherein the encounter information may include audio encounter information obtained from at least a first encounter participant (e.g., encounter participant 228, 226, 230, and/or 242). ACD process 10 may further be configured to process 302 the encounter information (e.g., machine vision encounter information 102 and/or audio encounter information 106) obtained from at least the first encounter participant, e.g., to generate an encounter transcript (e.g., encounter transcript 234) and/or generate 304 a user interface displaying a plurality of layers associated with the audio encounter information obtained from at least the first encounter participant. In some implementations, ACD process 10 may process at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

As noted above, ACD process 10 may process 302 the audio encounter information obtained from at least the first encounter participant. In some implementations, processing 302 the first audio encounter information may include defining 306 linkages between each of the plurality of layers associated with the audio encounter information. For example, the first layer of the plurality of layers may be an audio signal associated with the audio encounter information (e.g., complete audio of the encounter, encompassing and clearly delineating each participant), wherein the second layer of the plurality of layers may be a transcript associated with the audio encounter information (e.g., a diarized audio transcript (verbatim) for each participant in the encounter), and wherein the third layer of the plurality of layers may be a medical report associated with the audio encounter information (e.g., a draft medical report in the appropriate clinical output format). In some implementations, additional layers may include, e.g., the above-noted machine vision-based recording of the encounter, including various signal formats and features, and discrete, standardized, actionable data resulting from the encounter, including, but not limited to medication plans (for example, in RxNorm) or lab orders (for example, LOINC) or diagnoses (for example, ICD10, CPT etc). In the example, the signals captured from the encounter information may be processed 304 into at least the above-noted three separate, yet closely linked and interdependent layers.

In some implementations, ACD process 10 may include an ASR portion that may process 302 the audio encounter information producing an approximate (e.g., diarized) verbatim transcript along with alignment information indicating the audio interval corresponding to each transcript word. In some implementations, a deep learning (e.g., sequence to sequence) model associated with ACD process 10 may convert the transcript to a medical report. It will be appreciated that various attribution techniques may be employed by ACD process 10 that may effectively softly assign responsibility for a given output (e.g., medical report) word to input (e.g., conversation transcript) words (e.g. attention weights, integrated gradient, etc.) according to the model. As a result, this may provide a soft mapping from the transcript word positions to report word positions. In some implementations, the input word position assigned maximal attribution for a given output word may be interpreted as being aligned (linked) to that output (e.g., when a hard mapping is required). Based on the ASR time alignment, a word in the draft medical report, aligned to a word in the ASR conversation transcript, may now be associated with an audio time interval of the associated audio signal of the audio encounter information.

In some implementations, ACD process 10 may also may link (i.e., align) the ASR conversation transcript words with the draft medical report words. For transcript words that may have maximal attribution value for some set of medical report words, ACD process 10 may link them with the first word in that set. For the remaining transcript words, ACD process 10 may link them to the same word that the nearest preceding (or if none, nearest subsequent) conversation transcript word is linked to.

In some implementations, a visual recording (e.g., video stream of the patient encounter), if available, may also be a layer and may be time indexed and thus a given point in the recording may be associated with the same time in the audio recording and thus a conversation transcript word and draft report word. In some implementations, if discrete, standardized, actionable data is produced as a second (parallel) output sequence of the sequence to sequence model, then a similar model output attribution technique may be used to align tokens in this actionable data with the ASR conversation transcript words, and thus the audio intervals.

In some implementations, ACD process 10 may generate 304 a user interface displaying a plurality of layers associated with the audio encounter information obtained from at least the first encounter participant. For example, and referring at least to the example implementation of FIG. 5, an example user interface (e.g., user interface 500) is shown. It will be appreciated that UI 500 is shown merely for example purposes only, and that more or less features and arrangements of features may be used without departing from the scope of the present disclosure.

Figure 5:
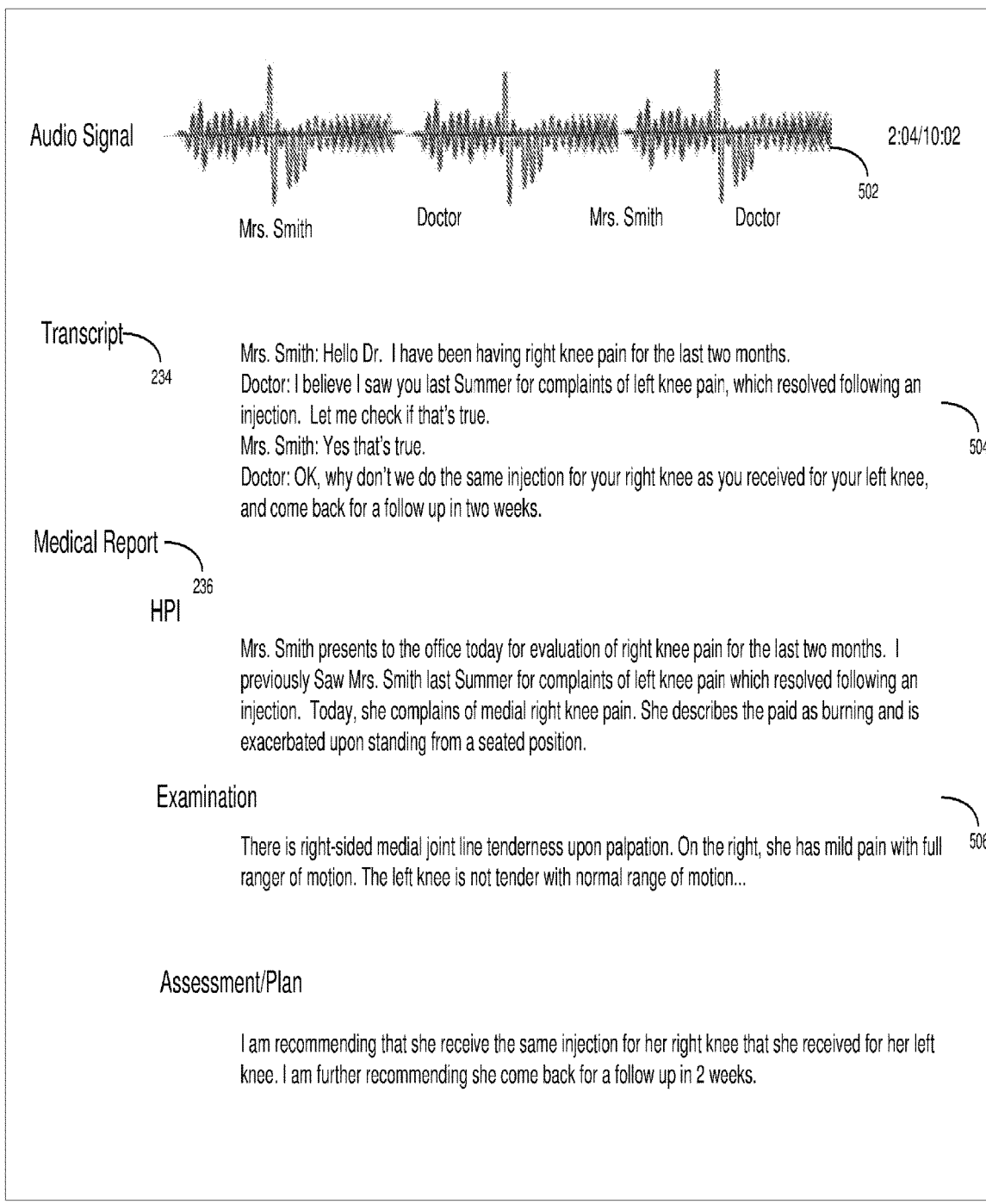
FIG. 5 is a user interface of the automated clinical documentation process of FIG. 1.

As can be seen from FIG. 5, UI 500 includes the first layer of the plurality of layers (e.g., first layer 502 which may be a visualization and/or direct play-back of an audio signal associated with the audio encounter information (e.g., complete audio of the encounter, encompassing and clearly delineating each participant), second layer 504 of the plurality of layers which may be a transcript (e.g., encounter transcript 234) associated with the audio encounter information (e.g., a diarized audio transcript (verbatim) for each participant in the encounter), and third layer 506 of the plurality of layers which may be a medical report (e.g., medical report/record 236) associated with the audio encounter information (e.g., a draft medical report in the appropriate clinical output format). It will be appreciated that that each layer (audio, transcript, draft report, etc.) may be rendered in multiple different ways, and in the most appropriate way for a given use/preference of the end-user. As such, the specific rendering of layers should be taken as example only and not to limit the scope of the disclosure.

As noted above, encounter transcript 234 (via second layer 504) and/or medical record/record 236 (via third layer 506) may be reviewed by a medical professional involved with the patient encounter (e.g., a visit to a doctor's office) to determine the accuracy of the same and/or make corrections to the same. For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Figure 6:
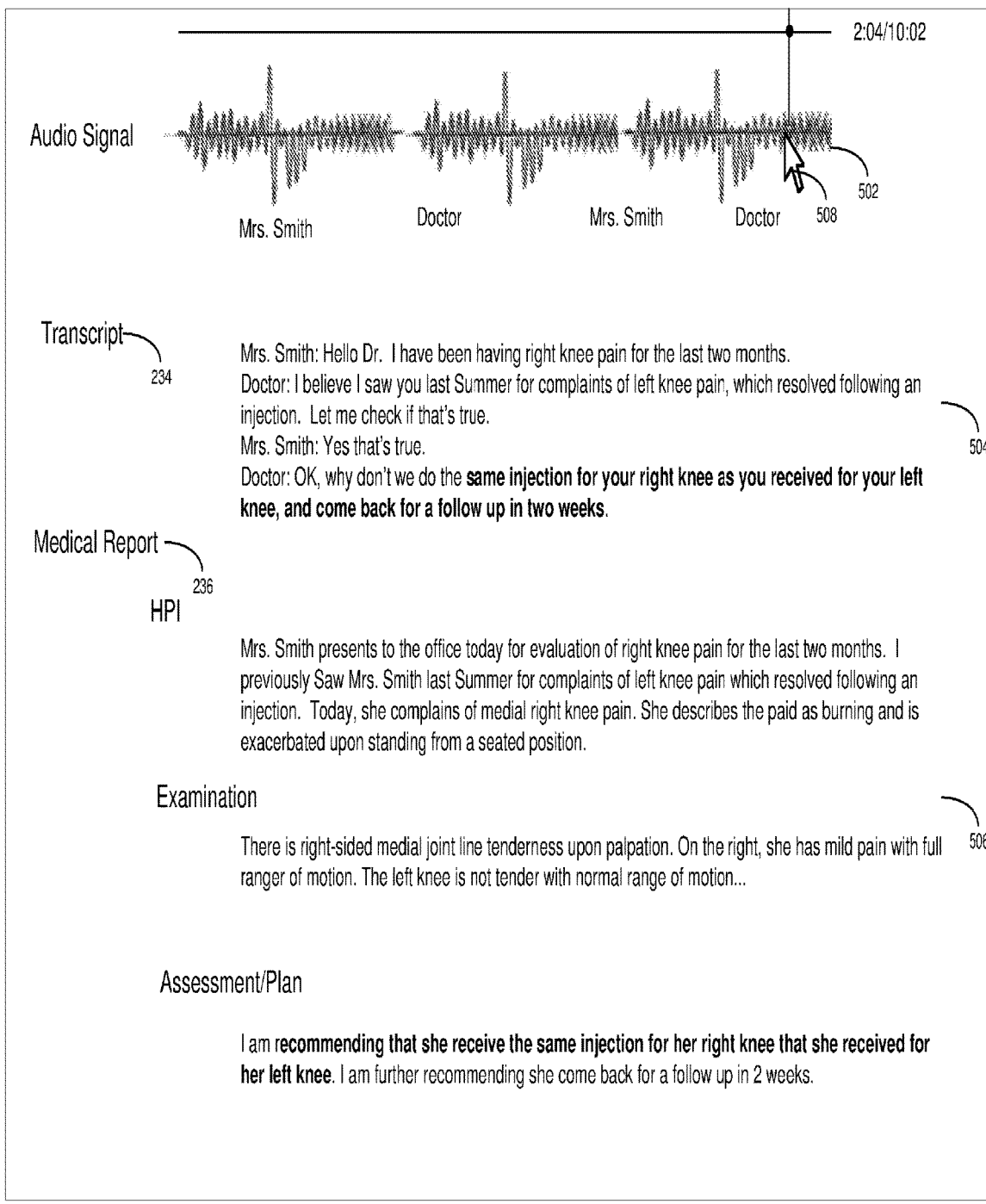
FIG. 6 is a user interface of the automated clinical documentation process of FIG. 1.
Figure 7:
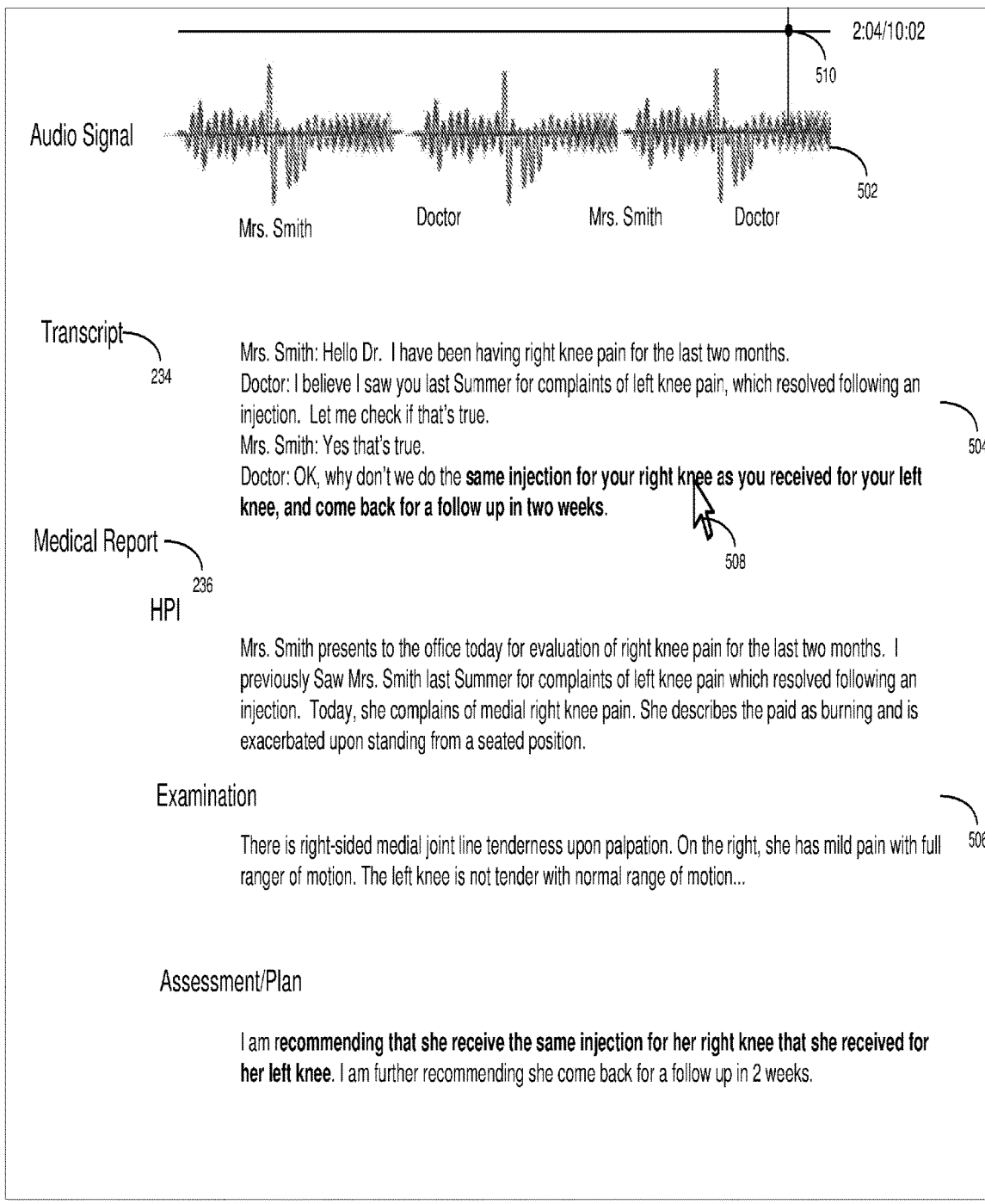
FIG. 7 is a user interface of the automated clinical documentation process of FIG. 1.
Figure 8:
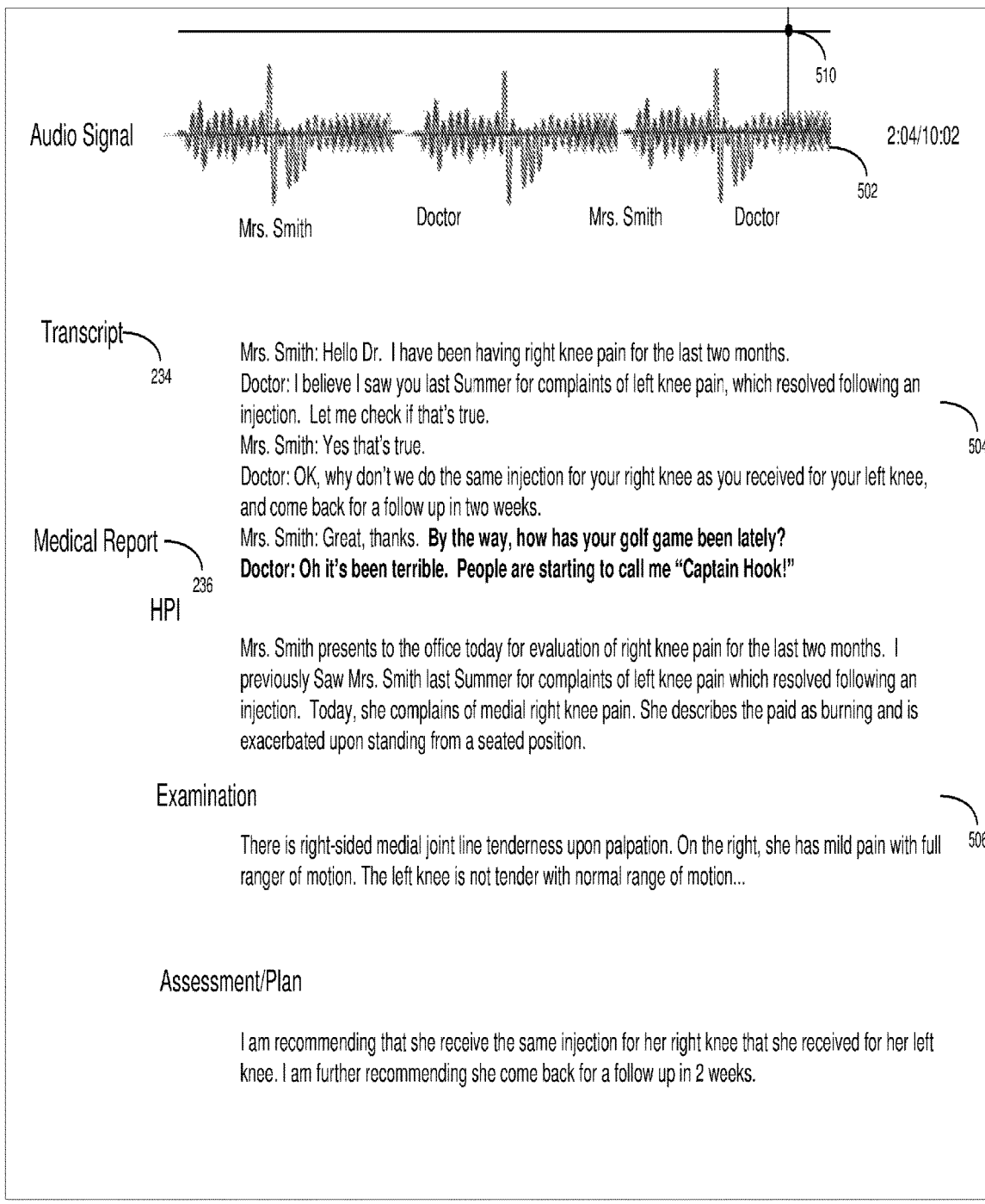
FIG. 8 is a user interface of the automated clinical documentation process of FIG. 1.

As such, and referring at least to the example implementation of FIG. 6, assume for example purposes only that a scribe is reviewing the encounter information using UI 500. In some implementations, ACD process 10 may receive 308 a selection of a first portion of the audio encounter information at a first layer of the plurality of layers on the user interface, and ACD process 10 may display 310 an annotation of at least one of a second layer of the plurality of layers and a third layer of the plurality of layers corresponding to the first portion of the audio encounter information of the first layer of the plurality of layers selected on the user interface. For instance, the scribe may use, e.g., cursor 508 or other known input techniques, to select a portion of first layer 502 (i.e., the audio information of the audio encounter information), which may be received 308 by ACD process 10. As a result, in some implementations, ACD process 10 may display 310 some kind of annotation of either the second layer (e.g., the portion of the transcript associated with the selected portion of the first layer) and/or the third layer (e.g., the portion of the medical report associated with the selected portion of the first layer). In the example, ACD process 10 has displayed an annotation (e.g., bold font) of the second layer (e.g., the portion of the transcript associated with the selected portion of the first layer) and the third layer (e.g., the portion of the medical report associated with the selected portion of the first layer). It will be appreciated that any type of annotation may be used (e.g., bold, italics, underline, highlights, shading, transparency, etc.) without departing from the scope of the present disclosure. As such, the use of bolding as the annotation should be taken as example only and not to otherwise limit the scope of the disclosure.

Similarly, in some implantations, ACD process 10 may receive 312 a selection of the first portion of the audio encounter information at one of the second layer of the plurality of layers and the third layer of the plurality of layers on the user interface, and ACD process 10 may provide 314 audio of the first layer corresponding to the first portion of the audio encounter information of one of the second layer of the plurality of layers and the third layer of the plurality of layers selected on the user interface. For example, and referring to the example implementation of FIG. 7, the scribe may use, e.g., cursor 508 or other known input techniques, to select a portion of second layer 504 (e.g., the transcript), and/or the third layer (e.g., the medical report) which may be received 312 by ACD process 10. As a result, in some implementations, ACD process 10 may provide 314 the audio of first layer 502 (e.g., the audio information of the audio encounter associated with the selected portion of second layer 504).

As such, ACD process 10 may leverage the above-noted defined linkages, such that the encounter recording as captured above may be provided to a human scribe (or physician) in such a fashion, so that they may navigate through each of these layers independently and be always in sync. For instance, if the scribe navigates through first layer 502 (audio) by listening, the part of the transcript that corresponds to that part of the audio may be bolded, highlighted, etc. accordingly, as well as the resulting medical report (and if relevant actionable data) from that information. Additionally/alternatively, if the scribe selects a part of the report, the audio/transcript sections that affected that part of the report may be bolded, highlighted, emphasized, etc. This annotation also may correspond to the audio and report "cursor" (e.g., audio cursor 510) moving, e.g., audio may next play from that position and typing/keyboard-navigation may commence from that position in the report. As a result, since each of the plurality of layers may be synchronized, a scribe (or physician, etc.) may later playback the whole patient encounter, navigate (e.g., "clicking" a mouse cursor of other pointing device at any position) in any portion of any of the layers, make edits, and would know which edit/correction belongs to the other sections (layers). More generally, "clicking" (i.e. resetting the cursor) in one viewed layer may annotate and update the cursor in the linked points/excerpts in the other layers.

In some implementations, at least a portion of the audio encounter information determined to lack relevance to the medical report may be one of sped up and skipped 316 by ACD process 10. For example, in some implementations, it may be possible for the scribe to "playback" the whole encounter and see the draft medical report "emerge" (or simply see each associated report words highlighted, in sync with the cursor) so that they may ascertain which signals from the encounter caused/triggered which parts of the report, and react (e.g., correct/edit, etc.) accordingly. However, ACD process 10 may sped up or skip 316 the audio not only where no speech is detected by the ASR portion of ACD process 10, but also where the model (e.g., sequence to sequence/abstractive summarization, etc.) does not attribute any significant responsibility for the draft report to that excerpt of the conversation transcript's aligned audio (e.g., accumulated attribution across all outputs (e.g., medical report text) for an input (e.g., ASR word/excerpt) being below some threshold). For instance, assume for example purposes only that Mrs. Smith (i.e., the patient in this example) asks the Doctor about his golf game, which the Doctor spends about 30 seconds discussing. In the example, ACD process 10 may determine that the discussion of the Doctor's golf game is not relevant for the draft report to that excerpt of the conversation transcript's aligned audio, and may either skip or speed up (fast forward) through that portion of the audio (and the associated transcript).

Similarly, at least a portion of the audio encounter information determined to lack relevance to the medical report may be annotated 318 by ACD process 10. For instance, and referring to the example implementation of FIG. 8, UI 500 is shown. In the example, ACD process 10 may annotate 318 the portion of the audio encounter information (e.g., transcript and/or medical report) where the model (e.g., sequence to sequence/abstractive summarization, etc.) model does not attribute any significant responsibility for the draft report to that excerpt of the conversation transcript's aligned audio. For instance, assume for example purposes only that Mrs. Smith (i.e., the patient in this example) asks the Doctor "By the way, how has your golf game been lately?", to which the Doctor replies "Oh it's been terrible. People are starting to call me "captain Hook!" In the example, ACD process 10 may determine that the discussion of the Doctor's golf game is not relevant for the draft report to that excerpt of the conversation transcript's aligned audio, and may annotate 318 (e.g., bold) that portion of the transcript. This may be especially advantageous for direct editing by a physician, who typically would not listen to the audio if reviewing/finalizing the report directly subsequent to the patient encounter. Thus, ACD process 10 may annotate 318 the subset of the transcript for which the model does not (significantly) attribute any portion of the medical report, allowing the physician to quickly scan for clinically relevant information potentially inadvertently missed by the model (e.g., not captured in some form in the report).

Figure 9:
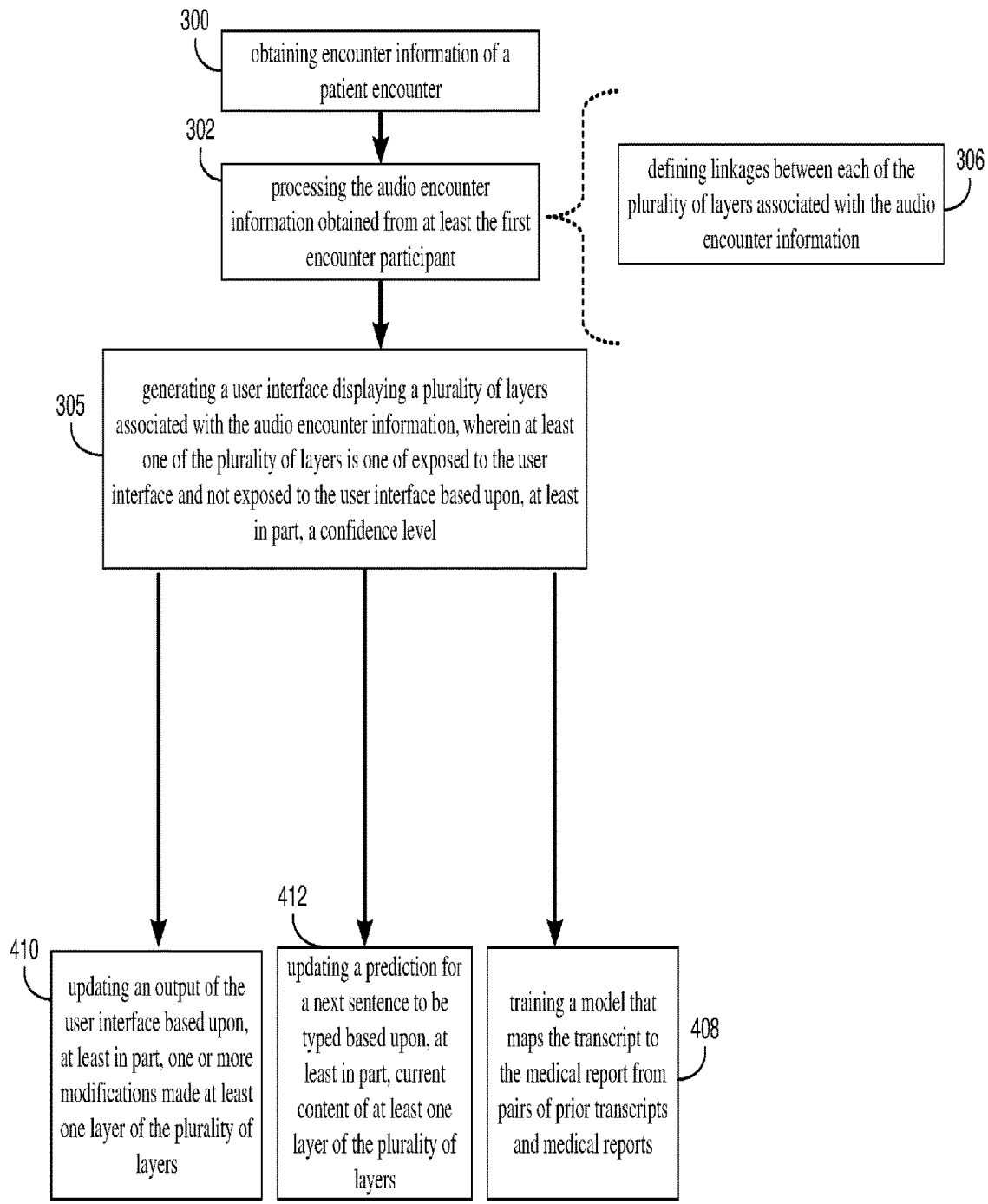
FIG. 9 is a flow chart of one implementation of the automated clinical documentation process of FIG. 1.

As discussed above, automated clinical documentation (ACD) process 10 may be configured to automate the collection and processing of clinical encounter information to generate/store/distribute medical records. Accordingly, as discussed above and referring also to at least to FIG. 9, ACD process 10 may be configured to obtain 300 encounter information (e.g., machine vision encounter information 102 and/or audio encounter information 106) of a patient encounter (e.g., a visit to a doctor's office) of at least a first encounter participant, wherein the encounter information may include audio encounter information obtained from at least a first encounter participant (e.g., encounter participant 228, 226, 230, and/or 242). ACD process 10 may further be configured to process 302 the encounter information (e.g., machine vision encounter information 102 and/or audio encounter information 106) obtained from at least the first encounter participant, e.g., to generate an encounter transcript (e.g., encounter transcript 234) and/or generate 305 a user interface displaying a plurality of layers associated with the audio encounter information obtained from at least the first encounter participant, wherein at least one of the plurality of layers is one of exposed to the user interface and not exposed to the user interface based upon, at least in part, a confidence level. In some implementations, ACD process 10 may process at least a portion of the encounter transcript (e.g., encounter transcript 234) to populate at least a portion of a medical record/report (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

In some implementations, processing 302 the first audio encounter information may include defining 306 linkages between each of the plurality of layers associated with the audio encounter information. For example, the first layer of the plurality of layers may be a visualization and/or direct play-back of an audio signal associated with the audio encounter information (e.g., complete audio of the encounter, encompassing and clearly delineating each participant), wherein the second layer of the plurality of layers may be a transcript associated with the audio encounter information (e.g., a diarized audio transcript (verbatim) for each participant in the encounter), and wherein the third layer of the plurality of layers may be a medical report associated with the audio encounter information (e.g., a draft medical report in the appropriate clinical output format). In some implementations, additional layers may include, e.g., the above-noted machine vision-based recording of the encounter, including various signal formats and features, and discrete, standardized, actionable data resulting from the encounter, including, but not limited to medication plans (for example, in RxNorm) or lab orders (for example, LOINC) or diagnoses (for example, ICD10, CPT etc). In the example, the signals captured from the encounter information may be processed 304 into at least the above-noted three separate, yet closely linked and interdependent layers.

In some implementations, ACD process 10 may include an ASR portion that may process 302 the audio encounter information producing an approximate (e.g., diarized) verbatim transcript along with alignment information indicating the audio interval corresponding to each transcript word. In some implementations, a deep learning (e.g., sequence to sequence) model associated with ACD process 10 may convert the transcript to a medical report. It will be appreciated that various attribution techniques may be employed by ACD process 10 that may effectively softly assign responsibility for a given output (e.g., medical report) word to input (e.g., conversation transcript) words (e.g. attention weights, integrated gradient, etc.) according to the model. As a result, this may provide a soft mapping from the transcript word positions to report word positions. In some implementations, the input word position assigned maximal attribution for a given output word may be interpreted as being aligned (linked) to that output (e.g., when a hard mapping is required). Based on the ASR time alignment, a word in the draft medical report, aligned to a word in the ASR conversation transcript, may now be associated with an audio time interval of the associated audio signal of the audio encounter information.

In some implementations, ACD process 10 may also may link (i.e., align) the ASR conversation transcript words with the draft medical report words. For transcript words that may have maximal attribution value for some set of medical report words, ACD process 10 may link them with the first word in that set. For the remaining transcript words, ACD process 10 may link them to the same word that the nearest preceding (or if none, nearest subsequent) conversation transcript word is linked to. As a result, since each of the plurality of layers may be synchronized, a scribe (or physician, etc.) may later playback the whole patient encounter, navigate in any of the layers, make edits, and would know which edit/correction belongs to the other sections (layers).

In some implementations, a visual recording (e.g., video stream of the patient encounter), if available, may also be a layer and may be time indexed and thus a given point in the recording may be associated with the same time in the audio recording and thus a conversation transcript word and draft report word. In some implementations, if discrete, standardized, actionable data is produced as a second (parallel) output sequence of the sequence to sequence model, then a similar model output attribution technique may be used to align tokens in this actionable data with the ASR conversation transcript words, and thus the audio intervals.

In some implementations, ACD process 10 may generate 305 a user interface displaying a plurality of layers associated with the audio encounter information obtained from at least the first encounter participant, wherein at least one of the plurality of layers is one of exposed to the user interface and not exposed to the user interface based upon, at least in part, a confidence level. For example, and referring again at least to the example implementation of FIG. 5, an example user interface (e.g., user interface 500) is shown. It will be appreciated that UI 500 is shown merely for example purposes only, and that more or less features and arrangements of features may be used without departing from the scope of the present disclosure.

As can be seen from FIG. 5, UI 500 includes the first layer of the plurality of layers (e.g., first layer 502 which may be a visualization and/or direct play-back of an audio signal associated with the audio encounter information (e.g., complete audio of the encounter, encompassing and clearly delineating each participant), second layer 504 of the plurality of layers which may be a transcript (e.g., encounter transcript 234) associated with the audio encounter information (e.g., a diarized audio transcript (verbatim) for each participant in the encounter), and third layer 506 of the plurality of layers which may be a medical report (e.g., medical report/record 236) associated with the audio encounter information (e.g., a draft medical report in the appropriate clinical output format). It will be appreciated that that each layer (audio, transcript, draft report, etc.) may be rendered in multiple different ways, and in the most appropriate way for a given use/preference of the end-user. As such, the specific rendering of layers should be taken as example only and not to limit the scope of the disclosure.

As noted above, encounter transcript 234 (via second layer 504) and/or medical record/record 236 (via third layer 506) may be reviewed by a medical professional involved with the patient encounter (e.g., a visit to a doctor's office) to determine the accuracy of the same and/or make corrections to the same. For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

As noted above, at least one of the plurality of layers is one of exposed to the user interface and not exposed to the user interface based upon, at least in part, a confidence level. For example, ACD process 10 may employ a confidence model that may only expose (e.g., display) at least one layer (e.g., the medical report layer 506 or a section of the medical report layer section) to the user interface if ACD process 10 (via the confidence model) determines there is sufficient confidence, such as a threshold confidence level, that the draft report (or draft report section) will be faster than being typed from scratch. For instance, exposing (e.g., displaying) the medical report/section to UI 500 (e.g., for editing) may enable the ability to change some incorrectly labeled terms/sentences, which may be faster than manually typing out the entire section from the beginning; however, if so many terms/sentences are incorrect (and therefore need to be changed), it may be faster to simply type out the entire section from the beginning, rather than making substantial changes to the draft report section. As such, in the example where ACD process 10 determines an estimated time that it will take to make corrections compared to an estimated time that it will take to type out the entire section from the beginning, and determines it may be faster to simply type out the entire section from the beginning (rather than make corrections), ACD process 10 may not display the report/section by not exposing the report/section to UI 500 in the first place. In some implementations, the use of the confidence level for exposure may be only for outputs expected to be part of the actual case record, e.g., the medical report layer and the optionally concurrently generated discrete/actionable structured data. In some implementations, the decision to expose or not expose may be per section of the medical report (or structured data), e.g., Exam section (report) or Lab Orders (structured), etc.

In some implementations, ACD process 10 may leverage various features of the confidence model, including the statistics (e.g., min, max, standard deviation, etc.) of the difference in probability between the first and second most likely word hypothesized at each position in the report/section via, e.g., a model (e.g., sequence to sequence model), the log likelihood of the draft report/section per the model (e.g., in addition to a length normalized version of this), confidence values from the ASR portion of ACD process 10 (e.g., particularly for segments to which the report/section content is attributed) and information regarding the typical (e.g., mean/standard deviation) number of edits required for a relevant physician and typical number of edits made by a relevant scribe. For draft reports/sections that ACD process 10 may actually expose to be edited (rather than typed from scratch), ACD process 10 may collect the number of edits made and time required to make them, which may be added to training and improvement of the confidence model over time.

For example, in some implementations, ACD process 10 may train 408 a model that maps the transcript to the medical report from pairs of prior transcripts and medical reports. For instance, the core model (e.g., sequence to sequence model) of ACD process 10 that may map the conversation transcript to the medical reports may be trained 408 from pairs of (e.g., ASR approximate) transcripts and medical reports. For example, as additional reports are generated/edited/typed by scribes/physicians, these additional reports may be automatically (or manually) added to the training pool for the sequence to sequence model, which may be automatically intermittently retrained. In some implementations, the model may be metadata-dependent (e.g., physician, institution, scribe, etc.), either by (e.g., regularized) adaptation to appropriate subsets of the training pool or by using this metadata as inputs or combination thereof. That is, the training pool may be specific to the user, type of user, or institution of the user making the changes to the medical report. In some implementations, the number and types of edits made by the scribe (or other user) may also be used by the confidence model to better predict the number of edits (and thus editing efficiency) for subsequent drafts.

In some implementations, e.g., towards the end of the patient encounter, as the confidence of the information regarding the medical report section rises, more items may be documented (e.g., added) in this section. For instance, assume for example purposes only that one of the encounter participants (e.g., the physician) mentions "examination." Using the techniques described above, ACD process 10 may recognize this fact, and may display some associated points about the physical examinations under the "Examination" section (e.g., in the medical report layer 506 shown at least in FIG. 5), which may be first grayed. In the example, as the physician continues to verbalize further associated points that make the confidence level of what was entered into the Examination section higher, the greyed points may become solid, and further adjustments/edits may be made by ACD process 10 shortly thereafter (e.g., in the following seconds). Similarly, related to the "Assessment/Plan" section (e.g., in the medical report layer 506) after the physician verbalizes his assessment, ACD process 10 may start documenting that section, first grayed, but then the grayed words may become more solid (e.g., darker or normal solid color) with more points being added as ACD process 10 knows more and the confidence level rises. In some implementations, showing the transition from grey to solid wording may help train scribes (or other users) to use ACD process 10 and recognize how it works.

In some implementations, ACD process 10 may update 410 an output of the user interface based upon, at least in part, one or more modifications made at least one layer of the plurality of layers. For instance, rather than the output being static during the editing process, ACD process 10 may update 410 the output based on the modifications made by the editor so far (e.g., based on the decoder being autoregressive in nature). In particular, the decoder (e.g., sequence to sequence decoder) output may depend on its preceding output. As such, if the scribe (or other user) makes a correction in one part of the draft report, ACD process 10 may update a best guess at the subsequent content. In some implementations, this may be distracting to the user, and so to make it less distracting, it may be optionally limited to a toggle-able mode (e.g., online/synchronous vs. global review mode) and/or limited to only modifying the draft output for subsequent sections of the report. In some implementations, there may be at least four ways that corrections to case-record-persistent system outputs (e.g., medical reports, structured data) may be utilized. For example, pairs of ASR transcripts and corrected reports may be used for offline (sequence to sequence, transcript→report) model training. If in the typing acceleration mode as opposed to draft-report-correction mode, as the user types, the prediction for next sentence may be updated, which may not be model training/adaptation, but rather a reflection of the (auto-regressive) model predicting next output based on report content so far. If in the draft-report-correction mode, as the user makes corrections, prediction of subsequent content (sentences or perhaps less distracting, sections) and thus the draft report content (in this report) may be updated, again utilizing the same auto-regressive nature of the sequence to sequence model (and not some result of model training). Tuples of ASR transcripts (along with ASR confidence information), draft reports and noted user edits (e.g., corrections) may be used for an offline confidence model (e.g., required number of edits) training.

In some implementations, ACD process 10 may update 412 a prediction for a next sentence to be typed based upon, at least in part, current content of at least one layer of the plurality of layers, where in some implementations, the at least one layer of the plurality of layers may be the medical report. For example, for reports that the above-noted confidence model (via ACD process 10) determines are best typed from scratch rather than editing a draft, ACD process 10 may leverage the summarization model to accelerate composition by having it predict the next sentence to type and updating that prediction based on, and to be consistent with, what the scribe (or other user) has typed so far. For instance, ACD process 10 (e.g., via UI 500) may allow the user to select the model's prediction of the current/next sentence being presented to the user in the report by selecting the tab key (or other shortcut) to complete the sentence (e.g., auto-completion based typing accelerant). In this way, ACD process 10 (e.g., via the model) may only predict the draft report a sentence at a time based on the scribes typing/feedback. In some implementations, the prediction may be based not just upon what the scribe is currently writing, but may additionally (or alternatively) be based upon the context of what the scribe has previous written in previous sentences of the report (or based upon a training pool specific to the scribe). In some implementations, the sentence prediction may be based on the same model that produces the draft medical report. In some implementations, when based on the confidence model and it is decided to suppress the draft medical report (section), the ACD process 10 based auto-completion typing accelerant may allow the salvage of some efficiency improvement.

Figure 10:
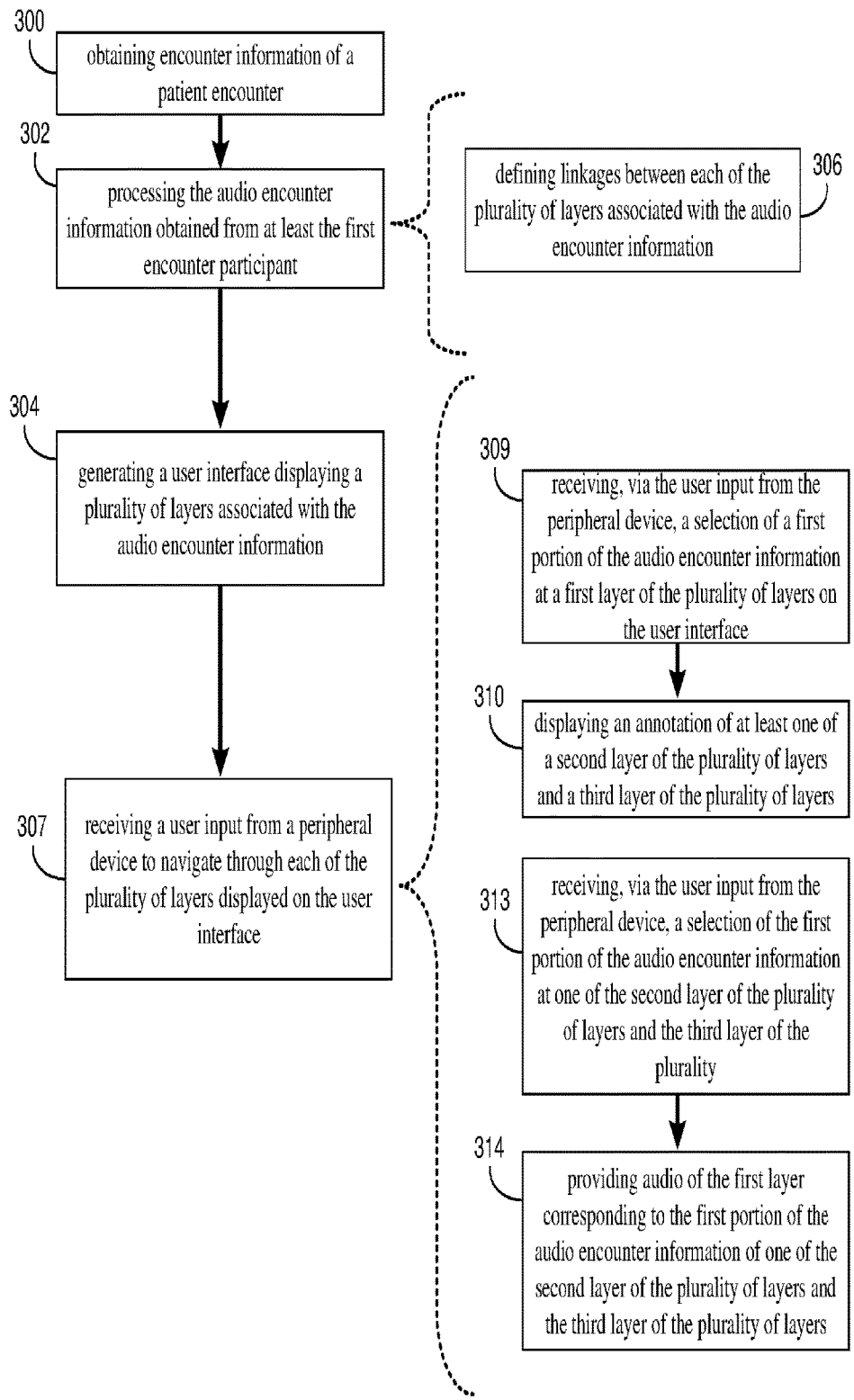
FIG. 10 is a flow chart of one implementation of the automated clinical documentation process of FIG. 1.

As discussed above, automated clinical documentation (ACD) process 10 may be configured to automate the collection and processing of clinical encounter information to generate/store/distribute medical records. Accordingly and referring also at least to FIGS. 10-11, ACD process 10 may be configured to obtain 300 encounter information (e.g., machine vision encounter information 102 and/or audio encounter information 106) of a patient encounter (e.g., a visit to a doctor's office) of at least a first encounter participant, wherein the encounter information may include audio encounter information obtained from at least a first encounter participant (e.g., encounter participant 228, 226, 230, and/or 242). ACD process 10 may further be configured to process 302 the encounter information (e.g., machine vision encounter information 102 and/or audio encounter information 106) obtained from at least the first encounter participant, e.g., to generate an encounter transcript (e.g., encounter transcript 234) and/or generate 304 a user interface displaying a plurality of layers associated with the audio encounter information obtained from at least the first encounter participant. In some implementations, ACD process 10 may receive 307 a user input from a peripheral device to navigate through each of the plurality of layers associated with the audio encounter information displayed on the user interface. In some implementations, ACD process 10 may process at least a portion of the encounter transcript (e.g., encounter transcript 234) to populate at least a portion of a medical record (e.g., medical record 236)

associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

As noted above, ACD process 10 may process 302 the audio encounter information obtained from at least the first encounter participant. In some implementations, processing 302 the first audio encounter information may include defining 306 linkages between each of the plurality of layers associated with the audio encounter information. For example, the first layer of the plurality of layers may be a visualization and/or direct play-back of an audio signal associated with the audio encounter information (e.g., complete audio of the encounter, encompassing and clearly delineating each participant), wherein the second layer of the plurality of layers may be a transcript associated with the audio encounter information (e.g., a diarized audio transcript (verbatim) for each participant in the encounter), and wherein the third layer of the plurality of layers may be a medical report associated with the audio encounter information (e.g., a draft medical report in the appropriate clinical output format). In some implementations, additional layers may include, e.g., the above-noted machine vision-based recording of the encounter, including various signal formats and features, and discrete, standardized, actionable data resulting from the encounter, including, but not limited to medication plans (for example, in RxNorm) or lab orders (for example, LOINC) or diagnoses (for example, ICD10, CPT etc). In the example, the signals captured from the encounter information may be processed 304 into at least the above-noted three separate, yet closely linked and interdependent layers.

In some implementations, ACD process 10 may include an ASR portion that may process 302 the audio encounter information producing an approximate (e.g., diarized) verbatim transcript along with alignment information indicating the audio interval corresponding to each transcript word. In some implementations, a deep learning (e.g., sequence to sequence) model associated with ACD process 10 may convert the transcript to a medical report. It will be appreciated that various attribution techniques may be employed by ACD process 10 that may effectively softly assign responsibility for a given output (e.g., medical report) word to input (e.g., conversation transcript) words (e.g. attention weights, integrated gradient, etc.) according to the model. As a result, this may provide a soft mapping from the transcript word positions to report word positions. In some implementations, the input word position assigned maximal attribution for a given output word may be interpreted as being aligned (linked) to that output (e.g., when a hard mapping is required). Based on the ASR time alignment, a word in the draft medical report, aligned to a word in the ASR conversation transcript, may now be associated with an audio time interval of the associated audio signal of the audio encounter information.

In some implementations, ACD process 10 may also may link (i.e., align) the ASR conversation transcript words with the draft medical report words. For transcript words that may have maximal attribution value for some set of medical report words, ACD process 10 may link them with the first word in that set. For the remaining transcript words, ACD process 10 may link them to the same word that the nearest preceding (or if none, nearest subsequent) conversation transcript word is linked to.

In some implementations, a visual recording (e.g., video stream of the patient encounter), if available, may also be a layer and may be time indexed and thus a given point in the recording may be associated with the same time in the audio recording and thus a conversation transcript word and draft report word. In some implementations, if discrete, standardized, actionable data is produced as a second (parallel) output sequence of the sequence to sequence model, then a similar model output attribution technique may be used to align tokens in this actionable data with the ASR conversation transcript words, and thus the audio intervals.

In some implementations, ACD process 10 may generate 304 a user interface displaying a plurality of layers associated with the audio encounter information obtained from at least the first encounter participant. For example, and referring again at least to the example implementation of FIG. 5, an example user interface (e.g., user interface 500) is shown. It will be appreciated that UI 500 is shown merely for example purposes only, and that more or less features and arrangements of features may be used without departing from the scope of the present disclosure.

As can be seen from FIG. 5, UI 500 includes the first layer of the plurality of layers (e.g., first layer 502 which may be a visualization and/or direct play-back of an audio signal associated with the audio encounter information (e.g., complete audio of the encounter, encompassing and clearly delineating each participant), second layer 504 of the plurality of layers which may be a transcript (e.g., encounter transcript 234) associated with the audio encounter information (e.g., a diarized audio transcript (verbatim) for each participant in the encounter), and third layer 506 of the plurality of layers which may be a medical report (e.g., medical report/record 236) associated with the audio encounter information (e.g., a draft medical report in the appropriate clinical output format). It will be appreciated that that each layer (audio, transcript, draft report, etc.) may be rendered in multiple different ways, and in the most appropriate way for a given use/preference of the end-user. As such, the specific rendering of layers should be taken as example only and not to limit the scope of the disclosure.

As noted above, encounter transcript 234 (via second layer 504) and/or medical record/record 236 (via third layer 506) may be reviewed by a medical professional involved with the patient encounter (e.g., a visit to a doctor's office) to determine the accuracy of the same and/or make corrections to the same. For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Figure 11:
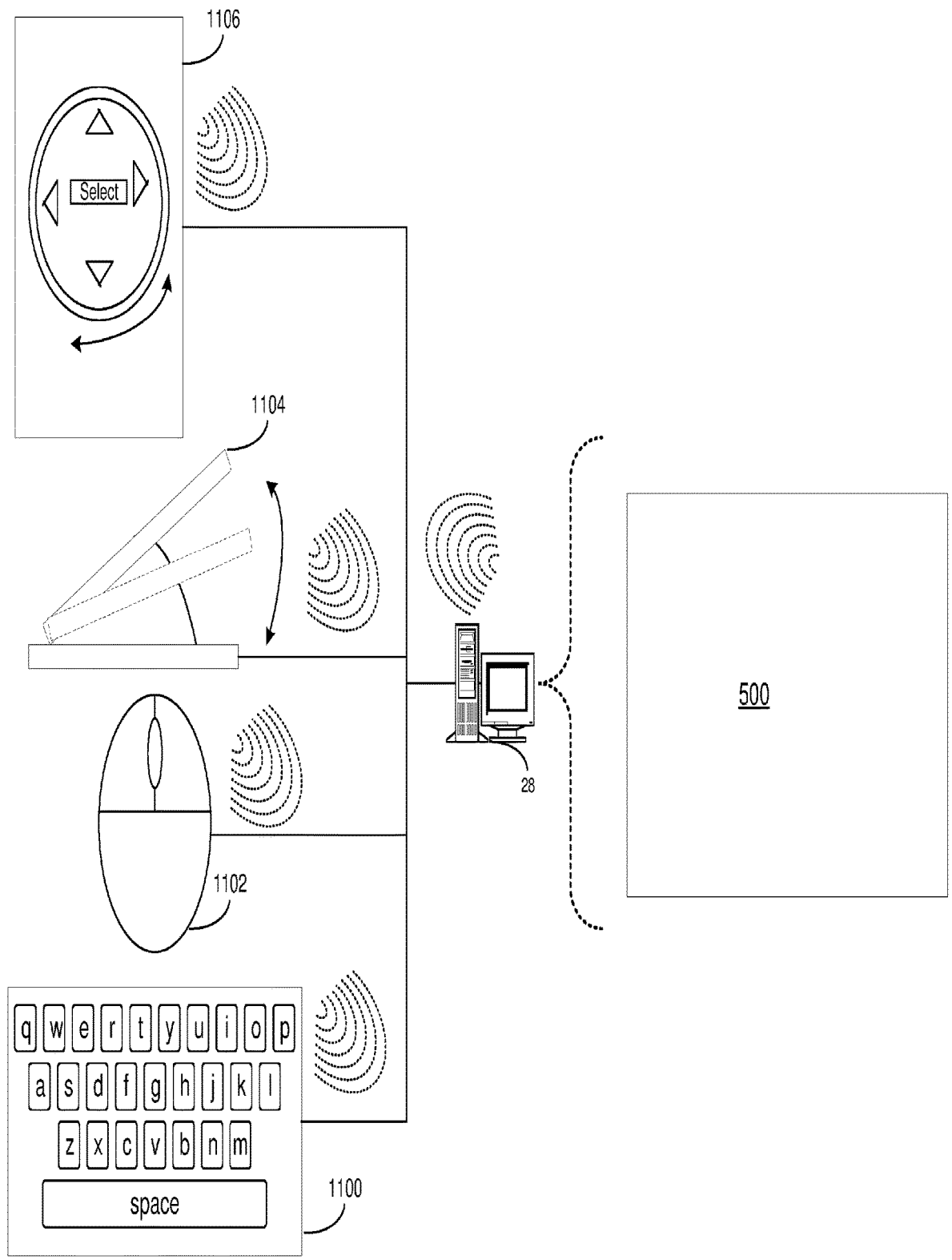
FIG. 11 is a diagrammatic view of example peripheral devices that may be used with the automated clinical documentation process of FIG. 1.

Therefore, and referring at least to the example implementation of FIG. 11, to help review encounter transcript 234 and/or medical record 236 to confirm that the same was accurate and/or make corrections to the same, in some implementations, ACD process 10 may receive 307 a user input from a peripheral device to navigate through each of the plurality of layers associated with the audio encounter information displayed on the user interface. In some implementations, the peripheral device may include, e.g., a keyboard (e.g., keyboard 1100), a pointing device (e.g., mouse 1102), a foot pedal (e.g., foot pedal 1104), a dial (e.g., dial 1106), or combination thereof. It will be appreciated that other peripheral devices may be used without departing from the scope of the present disclosure. One or more of the peripheral devices may be physically or wirelessly connected to the computing device displaying UI 500.

As such, and referring again at least to the example implementation of FIG. 6, assume for example purposes only that a scribe is reviewing the encounter information using UI 500. In some implementations, receiving 307 the user input from the peripheral device may include receiving 309, via the user input from the peripheral device, a selection of a first portion of the audio encounter information at a first layer of the plurality of layers on the user interface, and ACD process 10 may display 310 an annotation of at least one of a second layer of the plurality of layers and a third layer of the plurality of layers corresponding to the first portion of the audio encounter information of the first layer of the plurality of layers selected on the user interface. For instance, the scribe may use, e.g., any of the example peripheral devices, to select a portion of first layer 502 (i.e., the audio information of the audio encounter information), which may be received 309 by ACD process 10. As a result, in some implementations, ACD process 10 may display 310 some kind of annotation of either the second layer (e.g., the portion of the transcript associated with the selected portion of the first layer) and/or the third layer (e.g., the portion of the medical report associated with the selected portion of the first layer). In the example, ACD process 10 has displayed an annotation (e.g., bold font) of the second layer (e.g., the portion of the transcript associated with the selected portion of the first layer) and the third layer (e.g., the portion of the medical report associated with the selected portion of the first layer). It will be appreciated that any type of annotation may be used (e.g., bold, italics, underline, highlights, shading, transparency, etc.) without departing from the scope of the present disclosure. As such, the use of bolding as the annotation should be taken as example only and not to otherwise limit the scope of the disclosure.

Similarly, in some implantations, receiving 307 the user input from the peripheral device may include receiving 313, via the user input from the peripheral device, a selection of the first portion of the audio encounter information at one of the second layer of the plurality of layers and the third layer of the plurality of layers on the user interface, and ACD process 10 may provide 314 audio of the first layer corresponding to the first portion of the audio encounter information of one of the second layer of the plurality of layers and the third layer of the plurality of layers selected on the user interface. For example, and referring again at least to the example implementation of FIG. 7, the scribe may use, e.g., any of the example peripheral devices, to select a portion of second layer 504 (e.g., the transcript), and/or the third layer (e.g., the medical report) which may be received 312 by ACD process 10. As a result, in some implementations, ACD process 10 may provide 314 the audio of first layer 502 (e.g., the audio information of the audio encounter associated with the selected portion of second layer 504).

As noted above, the physician (or scribe) may need to verify the correctness of the medical report created by ACD process 10. This may involve, e.g., checking for correctness of each sentence/word in the medical report generated by looking for evidence in the conversation transcript (attribution), checking the correctness of the conversational transcript generated by an ASR) by listening to the audio segment. The use of dedicated hardware (e.g., a peripheral device) may be utilized by ACD process 10 to improve editing efficiency for medical transcriptionists/physicians, etc. to help navigate and browse (e.g., sentence by sentence) through the draft medical report, the associated conversation transcript excerpt, and/or associated audio file, annotated (e.g., highlighted, bolded, etc.) with its corresponding audio cued up for easy playback.

For example, in some implementations, the user input from the peripheral device may include a keyboard shortcut when the peripheral device is keyboard 1100. For example, default and/or user defined keyboard shortcuts may be used to interact with UI 500. For instance, a combination of keys (e.g., control+shift+S) may execute a particular command for UI 500. For instance, such a shortcut may cause UI 500 to, e.g., switch between sentences in an output of the medical report, switch between sections in the output of the medical report, switch between the medical report and the transcript, provide/playback audio of the audio signal, cease/stop playback of the audio of the audio signal, speeding up playback of the audio of the audio signal, or slow down playback of the audio of the audio signal. It will be appreciated that various other keyboard shortcuts, as well as single key inputs (e.g., arrows, spacebar, etc.) may execute the above-noted commands for UI 500 without departing from the scope of the disclosure.

In some implementations, the user input from the peripheral device may include a pointing device action when the peripheral device is pointing device 1102. For example, default and/or user defined mouse actions may be used to interact with UI 500. For instance, movement of the mouse cursor over a particular portion of one of the above-noted layers, clicking or double clicking on a particular portion of one of the above-noted layers, hovering over a particular portion of one of the above-noted layers, using a scroll wheel of the mouse, etc. may execute a particular command for UI 500. For instance, any one of the example uses of the mouse may cause UI 500 to, e.g., switch between sentences in an output of the medical report, switch between sections in the output of the medical report, switch between the medical report and the transcript, provide/playback audio of the audio signal, cease/stop playback of the audio of the audio signal, speeding up playback of the audio of the audio signal, or slow down playback of the audio of the audio signal. It will be appreciated that various other keyboard shortcuts, as well as single key inputs (e.g., arrows, spacebar, etc.) may execute the above-noted commands for UI 500 without departing from the scope of the disclosure.

In some implementations, the user input from the peripheral device may include raising and lowering of the foot pedal when the peripheral device is foot pedal 1104. For example, default and/or user defined foot pedal actions may be used to interact with UI 500. For instance, raising and lowering of the foot pedal (similar to how the foot pedal in a vehicle may function) may execute a particular command for UI 500. For instance, lowering the pedal (e.g., using the user's foot to press down on pedal 1104) may cause UI 500 to, e.g., provide/playback audio of the audio signal, and may speed up playback of the audio of the audio signal depending on the amount the pedal is lowered. Conversely, raising the pedal (e.g., lifting the user's foot off the pedal 1104) may cause UI 500 to, e.g., cease/stop playback of the audio of the audio signal, and may or slow down playback of the audio of the audio signal depending on the amount the pedal is raised.

In some implementations, the user input from the peripheral device may include at least one of a rotating action, an up action, a down action, a left action, a right action, and a pressing action of the dial when the peripheral device is dial 1106. For example, default and/or user defined dial actions may be used to interact with UI 500. For instance, UI 500 (via ACD process 10) may switch the focus between sentences in the output medical report by rotating the dial, e.g., one click clockwise may move the focus to the next sentence and counter clockwise may move the focus to the previous sentence. As another example, UI 500 (via ACD process 10) may switch the focus between different sections of the medical report using the up/down arrows on dial 1106. Similarly, as discussed above at least with regard to FIGS. 6 and 7, evidence in conversational transcripts for the selected sentence in the report/transcript may be annotated (e.g., highlighted, bolded, etc.). Evidence may include a word or phrase or sentence and may be obtained from attention weights (e.g., byproduct of a sequence to sequence based summarization system) or other dedicated models for attribution. As another example, UI 500 (via ACD process 10) may switch focus from the medical report to the conversational transcript using, e.g., left/right arrows on dial 1106. As another example, UI 500 (via ACD process 10) may browse may switch the focus between sentences in the transcript by rotating the dial, e.g., one click clockwise may move the focus to the next sentence and counter clockwise may move the focus to the previous sentence. As yet another example, UI 500 (via ACD process 10) may, when the annotated sentence in the transcript is selected by pressing dial 1106, play back the corresponding audio chunk (e.g., identified by time stamps from the ASR decoding).

It will be appreciated that any of the example peripheral devices may be used in any combination with each other's functions without departing from the scope of the disclosure. For example, using pointing device 1102 to hover over a particular portion of the transcript, medical report section, or audio signal may be the starting location where, the functions of e.g., dial 1106 may be used. As such, the use of any particular peripheral device and its particular function should be taken as example only and not to otherwise limit the scope of the disclosure.

As such, ACD process 10 may leverage the above-noted defined linkages and peripheral devices, such that the encounter recording as captured above may be provided to a human scribe (or physician) in such a fashion, so that they may navigate through each of these layers independently and be always in sync. For instance, if the scribe navigates through first layer 502 (audio) by listening, the part of the transcript that corresponds to that part of the audio may be bolded, highlighted, etc. accordingly, as well as the resulting medical report (and if relevant actionable data) from that information. Additionally/alternatively, if the scribe selects a part of the report, the audio/transcript sections that affected that part of the report may be bolded, highlighted, emphasized, etc. This annotation also may correspond to the audio and report "cursor" (e.g., audio cursor 510) moving, e.g., audio may next play from that position and typing/keyboard-navigation may commence from that position in the report.

As a result, since each of the plurality of layers may be synchronized, a scribe (or physician, etc.) may later playback the whole patient encounter, navigate (e.g., "clicking" a mouse cursor of other pointing device at any position) in any portion of any of the layers, make edits, and would know which edit/correction belongs to the other sections (layers). More generally, "clicking" (i.e. resetting the cursor) in one viewed layer may annotate and update the cursor in the linked points/excerpts in the other layers.

Figure 12:
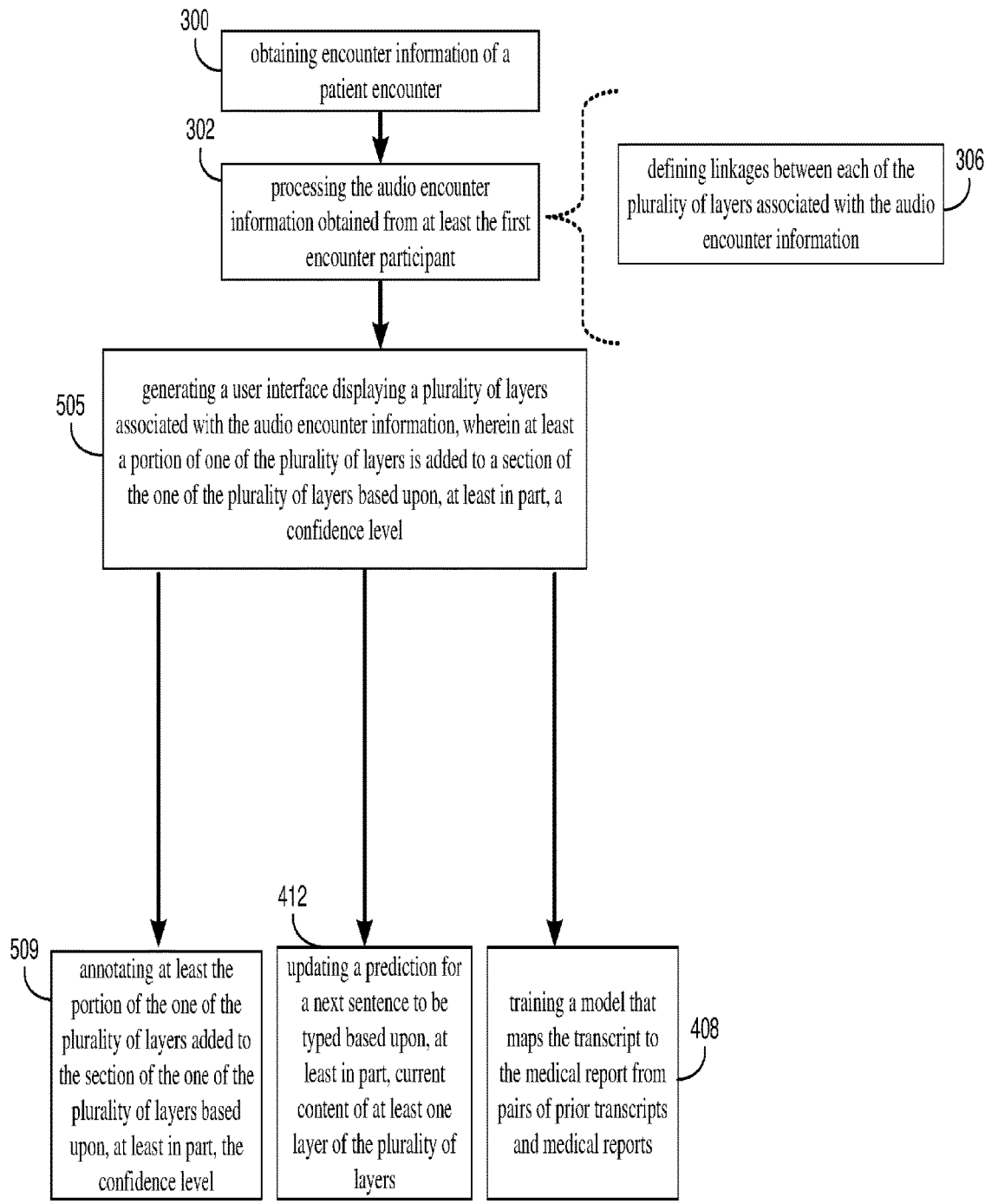
FIG. 12 is a flow chart of one implementation of the automated clinical documentation process of FIG. 1.
Figure 13:
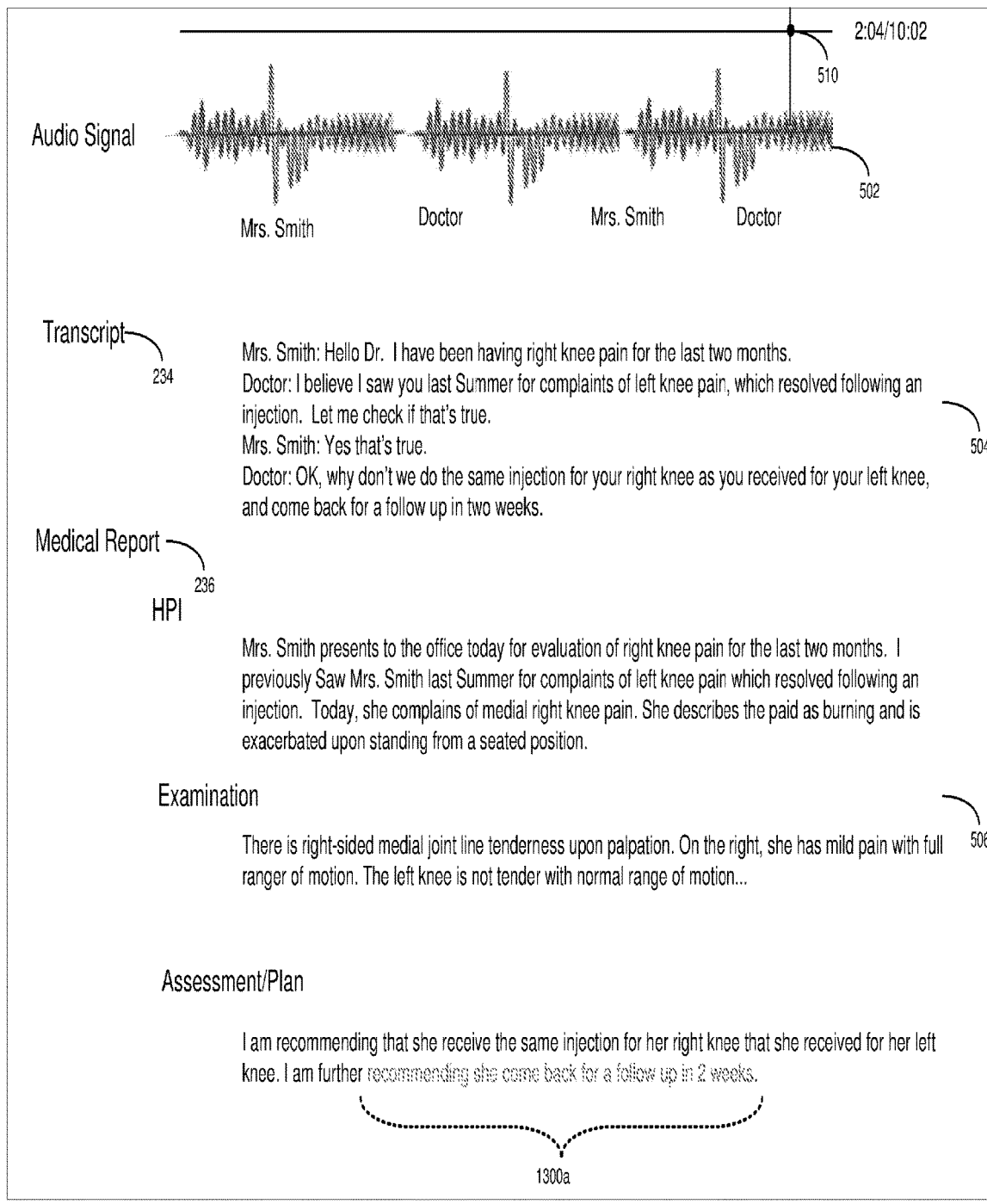
FIG. 13 is a user interface of the automated clinical documentation process of FIG. 1.
Figure 14:
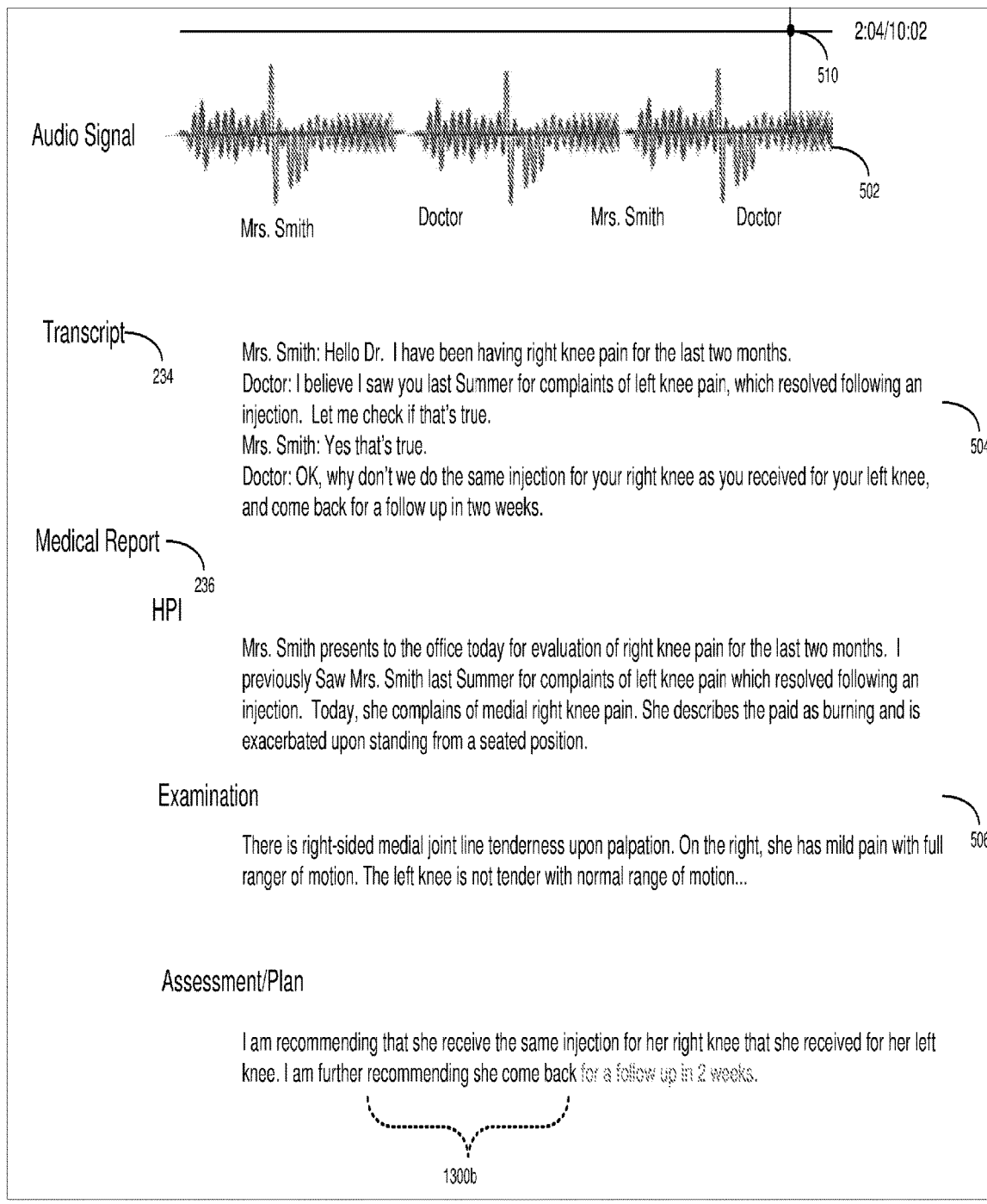
FIG. 14 is a user interface of the automated clinical documentation process of FIG. 1.

As discussed above, automated clinical documentation (ACD) process 10 may be configured to automate the collection and processing of clinical encounter information to generate/store/distribute medical records. Accordingly, as discussed above and referring also at least to FIGS. 12-14, ACD process 10 may be configured to obtain 300 encounter information (e.g., machine vision encounter information 102 and/or audio encounter information 106) of a patient encounter (e.g., a visit to a doctor's office) of at least a first encounter participant, wherein the encounter information may include audio encounter information obtained from at least a first encounter participant (e.g., encounter participant 228, 226, 230, and/or 242). ACD process 10 may further be configured to process 302 the encounter information (e.g., machine vision encounter information 102 and/or audio encounter information 106) obtained from at least the first encounter participant, e.g., to generate an encounter transcript (e.g., encounter transcript 234) and/or generate 505 a user interface displaying a plurality of layers associated with the audio encounter information obtained from at least the first encounter participant, wherein at least a portion of one of the plurality of layers is added to a section of the one of the plurality of layers based upon, at least in part, a confidence level. In some implementations, ACD process 10 may process at least a portion of the encounter transcript (e.g., encounter transcript 234) to populate at least a portion of a medical record/report (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

In some implementations, processing 302 the first audio encounter information may include defining 306 linkages between each of the plurality of layers associated with the audio encounter information. For example, the first layer of the plurality of layers may be a visualization and/or direct play-back of an audio signal associated with the audio encounter information (e.g., complete audio of the encounter, encompassing and clearly delineating each participant), wherein the second layer of the plurality of layers may be a transcript associated with the audio encounter information (e.g., a diarized audio transcript (verbatim) for each participant in the encounter), and wherein the third layer of the plurality of layers may be a medical report associated with the audio encounter information (e.g., a draft medical report in the appropriate clinical output format). In some implementations, additional layers may include, e.g., the above-noted machine vision-based recording of the encounter, including various signal formats and features, and discrete, standardized, actionable data resulting from the encounter, including, but not limited to medication plans (for example, in RxNorm) or lab orders (for example, LOINC) or diagnoses (for example, ICD10, CPT etc). In the example, the signals captured from the encounter information may be processed 304 into at least the above-noted three separate, yet closely linked and interdependent layers.

In some implementations, ACD process 10 may include an ASR portion that may process 302 the audio encounter information producing an approximate (e.g., diarized) verbatim transcript along with alignment information indicating the audio interval corresponding to each transcript word. In some implementations, a deep learning (e.g., sequence to sequence) model associated with ACD process 10 may convert the transcript to a medical report. It will be appreciated that various attribution techniques may be employed by ACD process 10 that may effectively softly assign responsibility for a given output (e.g., medical report) word to input (e.g., conversation transcript) words (e.g. attention weights, integrated gradient, etc.) according to the model. As a result, this may provide a soft mapping from the transcript word positions to report word positions. In some implementations, the input word position assigned maximal attribution for a given output word may be interpreted as being aligned (linked) to that output (e.g., when a hard mapping is required). Based on the ASR time alignment, a word in the draft medical report, aligned to a word in the ASR conversation transcript, may now be associated with an audio time interval of the associated audio signal of the audio encounter information.

In some implementations, ACD process 10 may also may link (i.e., align) the ASR conversation transcript words with the draft medical report words. For transcript words that may have maximal attribution value for some set of medical report words, ACD process 10 may link them with the first word in that set. For the remaining transcript words, ACD process 10 may link them to the same word that the nearest preceding (or if none, nearest subsequent) conversation transcript word is linked to. As a result, since each of the plurality of layers may be synchronized, a scribe (or physician, etc.) may later playback the whole patient encounter, navigate in any of the layers, make edits, and would know which edit/correction belongs to the other sections (layers).

In some implementations, a visual recording (e.g., video stream of the patient encounter), if available, may also be a layer and may be time indexed and thus a given point in the recording may be associated with the same time in the audio recording and thus a conversation transcript word and draft report word. In some implementations, if discrete, standardized, actionable data is produced as a second (parallel) output sequence of the sequence to sequence model, then a similar model output attribution technique may be used to align tokens in this actionable data with the ASR conversation transcript words, and thus the audio intervals.

As noted above, in some implementations, ACD process 10 may generate a user interface displaying a plurality of layers associated with the audio encounter information obtained from at least the first encounter participant. For example, and referring again at least to the example implementation of FIG. 5, an example user interface (e.g., user interface 500) is shown. It will be appreciated that UI 500 is shown merely for example purposes only, and that more or less features and arrangements of features may be used without departing from the scope of the present disclosure.

As can be seen from FIG. 5, UI 500 includes the first layer of the plurality of layers (e.g., first layer 502 which may be a visualization and/or direct play-back of an audio signal associated with the audio encounter information (e.g., complete audio of the encounter, encompassing and clearly delineating each participant), second layer 504 of the plurality of layers which may be a transcript (e.g., encounter transcript 234) associated with the audio encounter information (e.g., a diarized audio transcript (verbatim) for each participant in the encounter), and third layer 506 of the plurality of layers which may be a medical report (e.g., medical report/record 236) associated with the audio encounter information (e.g., a draft medical report in the appropriate clinical output format). It will be appreciated that that each layer (audio, transcript, draft report, etc.) may be rendered in multiple different ways, and in the most appropriate way for a given use/preference of the end-user. As such, the specific rendering of layers should be taken as example only and not to limit the scope of the disclosure.

As noted above, encounter transcript 234 (via second layer 504) and/or medical record/record 236 (via third layer 506) may be reviewed by a medical professional involved with the patient encounter (e.g., a visit to a doctor's office) to determine the accuracy of the same and/or make corrections to the same. For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

As noted above, at least one of the plurality of layers may be one of exposed to the user interface and not exposed to the user interface based upon, at least in part, a confidence level. For example, ACD process 10 may employ a confidence model that may only expose (e.g., display) at least one layer (e.g., the medical report layer 506 or a section of the medical report layer section) to the user interface if ACD process 10 (via the confidence model) determines there is sufficient confidence, such as a threshold confidence level, that the draft report (or draft report section) will be faster than being typed from scratch. For instance, exposing (e.g., displaying) the medical report/section to UI 500 (e.g., for editing) may enable the ability to change some incorrectly labeled terms/sentences, which may be faster than manually typing out the entire section from the beginning; however, if so many terms/sentences are incorrect (and therefore need to be changed), it may be faster to simply type out the entire section from the beginning, rather than making substantial changes to the draft report section. As such, in the example where ACD process 10 determines an estimated time that it will take to make corrections compared to an estimated time that it will take to type out the entire section from the beginning, and determines it may be faster to simply type out the entire section from the beginning (rather than make corrections), ACD process 10 may not display the report/section by not exposing the report/section to UI 500 in the first place.

In some implementations, ACD process 10 may leverage various features of the confidence model, including the statistics (e.g., min, max, standard deviation, etc.) of the difference in probability between the first and second most likely word hypothesized at each position in the report/section via, e.g., a model (e.g., sequence to sequence model), the log likelihood of the draft report/section per the model (e.g., in addition to a length normalized version of this), confidence values from the ASR portion of ACD process 10 (e.g., particularly for segments to which the report/section content is attributed) and information regarding the typical (e.g., mean/standard deviation) number of edits required for a relevant physician and typical number of edits made by a relevant scribe. For draft reports/sections that ACD process 10 may actually expose to be edited (rather than typed from scratch), ACD process 10 may collect the number of edits made and time required to make them, which may be added to training and improvement of the confidence model over time.

For example, in some implementations, ACD process 10 may train 408 a model that maps the transcript to the medical report from pairs of prior transcripts and medical reports. For instance, the core model (e.g., sequence to sequence model) of ACD process 10 that may map the conversation transcript to the medical reports may be trained 408 from pairs of (e.g., ASR approximate) transcripts and medical reports. For example, as additional reports are generated/edited/typed by scribes/physicians, these additional reports may be automatically (or manually) added to the training pool for the sequence to sequence model, which may be automatically intermittently retrained. In some implementations, the model may be metadata-dependent (e.g., physician, institution, scribe, etc.), either by (e.g., regularized) adaptation to appropriate subsets of the training pool or by using this metadata as inputs or combination thereof. That is, the training pool may be specific to the user, type of user, or institution of the user making the changes to the medical report. In some implementations, the number and types of edits made by the scribe (or other user) may also be used by the confidence model to better predict the number of edits (and thus editing efficiency) for subsequent drafts.

As noted above, in some implementations, ACD process 10 generate 505 UI 500 displaying the plurality of layers associated with the audio encounter information obtained from at least the first encounter participant, and in some implementations, ACD process 10 may annotate 509 at least the portion of the one of the plurality of layers added to the section of the one of the plurality of layers based upon, at least in part, the confidence level. For example, in some implementations, e.g., during a patient encounter, toward the end of the patient encounter, or during scribe training during playback, as the confidence of the information regarding the medical report section rises, more items may be documented (e.g., added) in this section. For instance, assume for example purposes only that one of the encounter participants (e.g., the physician) mentions "assessment" or "plan" or alternatively ACD process 10 may use NLU to determine from the conversational transcript 234 that the context of what the physician is saying (e.g., "and come back for a follow up in two weeks") may apply to the "Assessment/Plan" section (e.g., in medical report layer 506) of medical report 236. Using the techniques described above, ACD process 10 may recognize this, and may add (display) some associated points about the recommendation under the "Assessment/Plan" section (e.g., in the medical report layer 506 shown at least in the example implementation of UI 500 in FIG. 13), which may be first added and grayed based upon a first confidence level of what was said. That is, "recommending she come back for a follow up in 2 weeks" (shown at portion 1300*a*) may be first be added and grayed based upon the first confidence level being below a threshold confidence level. In the example, and referring at least to the example implementation of UI 500 shown in FIG. 14, as the physician continues to verbalize further associated points of what was respectively entered into the Assessment/Plan section, which therefore makes the confidence level (e.g., an updated confidence level above the threshold confidence level) of what was entered become higher, some of the grayed points (e.g., "recommending she come back" shown at portion 1300*b*) associated with the higher confidence level may be annotated (e.g., become solid or other type of annotation), or further adjustments/edits may be made by ACD process 10 shortly thereafter (e.g., in the following seconds) to correct the grayed portion based on the confidence level now taking into account the additional context of the further verbalization, which may then become solid. As such, after the physician verbalizes his assessment, ACD process 10 may start documenting that section, first grayed, but then the grayed words may become more solid (e.g., darker or normal solid color) with more points being added and becoming more solid as ACD process 10 knows more and the confidence level of what was said rises. In some implementations, showing the transition from gray to solid (or other annotation) wording may help train scribes (or other users) to use ACD process 10 and recognize how it works; however, it will be appreciated that the annotation of wording based upon confidence level may occur at any stage of the patient encounter and/or post patient encounter during scribe/physician playback/editing.

In some implementations, ACD process 10 may update 410 an output of the user interface based upon, at least in part, one or more modifications made at least one layer of the plurality of layers. For instance, rather than the output being static during the editing process, ACD process 10 may update 410 the output based on the modifications made by the editor so far (e.g., based on the decoder being autoregressive in nature). In particular, the decoder (e.g., sequence to sequence decoder) output may depend on its preceding output. As such, if the scribe (or other user) makes a correction in one part of the draft report, ACD process 10 may update a best guess at the subsequent content. In some implementations, this may be distracting to the user, and so to make it less distracting, it may be optionally limited to a toggle-able mode (e.g., online/synchronous vs. global review mode) and/or limited to only modifying the draft output for subsequent sections of the report.

In some implementations, ACD process 10 may update 412 a prediction for a next sentence to be typed based upon, at least in part, current content of at least one layer of the plurality of layers, where in some implementations, the at least one layer of the plurality of layers may be the medical report. For example, for reports that the above-noted confidence model (via ACD process 10) determines are best typed from scratch rather than editing a draft, ACD process 10 may leverage the summarization model to accelerate composition by having it predict the next sentence to type and updating that prediction based on, and to be consistent with, what the scribe (or other user) has typed so far. For instance, ACD process 10 (e.g., via UI 500) may allow the user to select the model's prediction of the current/next sentence being presented to the user in the report by selecting the tab key (or other shortcut) to complete the sentence. In this way, ACD process 10 (e.g., via the model) may only predict the draft report a sentence at a time based on the scribes typing/feedback. In some implementations, the prediction may be based not just upon what the scribe is currently writing, but may additionally (or alternatively) be based upon the context of what the scribe has previous written in previous sentences of the report (or based upon a training pool specific to the scribe).

Figure 15:
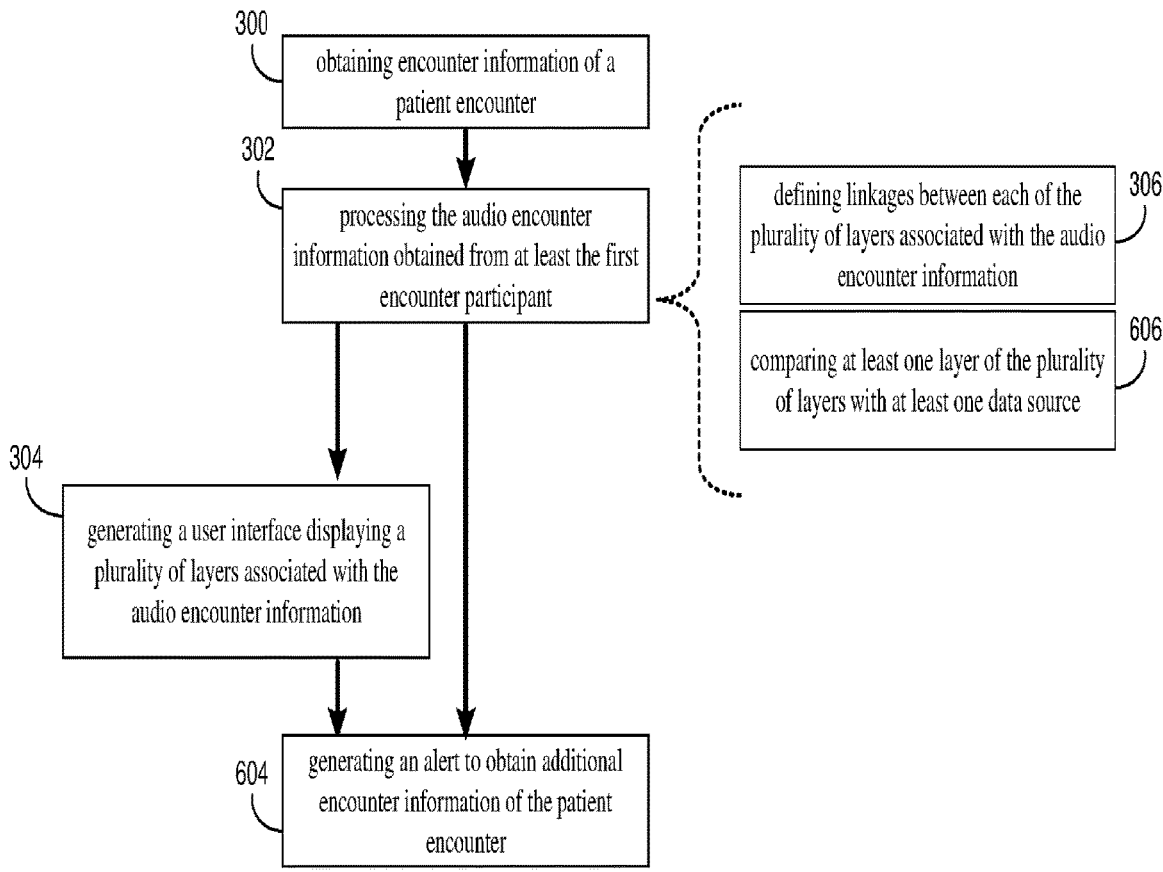
FIG. 15 is a flow chart of another implementation of the automated clinical documentation process of FIG. 1.

As discussed above, automated clinical documentation (ACD) process 10 may be configured to automate the collection and processing of clinical encounter information to generate/store/distribute medical records. Additionally, as discussed above and referring also at least to the example implementation of FIG. 15, ACD process 10 may be configured to obtain 300 encounter information (e.g., machine vision encounter information 102 and/or audio encounter information 106) of a patient encounter (e.g., a visit to a doctor's office) of at least a first encounter participant, wherein the encounter information may include audio encounter information obtained from at least a first encounter participant (e.g., encounter participant 228, 226, 230, and/or 242). ACD process 10 may further be configured to process 302 the encounter information (e.g., machine vision encounter information 102 and/or audio encounter information 106) obtained from at least the first encounter participant, e.g., generate 602 an alert to obtain additional encounter information of the patient encounter, to generate an encounter transcript (e.g., encounter transcript 234) and/or generate 304 a user interface displaying a plurality of layers associated with the audio encounter information obtained from at least the first encounter participant. In some implementations, ACD process 10 may process at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

As noted above, ACD process 10 may process 302 the audio encounter information obtained from at least the first encounter participant. In some implementations, processing 302 the first audio encounter information may include defining 306 linkages between each of the plurality of layers associated with the audio encounter information. For example, the first layer of the plurality of layers may be a visualization and/or direct play-back of an audio signal associated with the audio encounter information (e.g., complete audio of the encounter, encompassing and clearly delineating each participant), wherein the second layer of the plurality of layers may be a transcript associated with the audio encounter information (e.g., a diarized audio transcript (verbatim) for each participant in the encounter), and wherein the third layer of the plurality of layers may be a medical report associated with the audio encounter information (e.g., a draft medical report in the appropriate clinical output format). In some implementations, additional layers may include, e.g., the above-noted machine vision-based recording of the encounter, including various signal formats and features, and discrete, standardized, actionable data resulting from the encounter, including, but not limited to medication plans (for example, in RxNorm) or lab orders (for example, LOINC) or diagnoses (for example, ICD10, CPT etc). In the example, the signals captured from the encounter information may be processed 304 into at least the above-noted three separate, yet closely linked and interdependent layers.

In some implementations, ACD process 10 may include an ASR portion that may process 302 the audio encounter information producing an approximate (e.g., diarized) verbatim transcript along with alignment information indicating the audio interval corresponding to each transcript word. In some implementations, a deep learning (e.g., sequence to sequence) model associated with ACD process 10 may convert the transcript to a medical report. It will be appreciated that various attribution techniques may be employed by ACD process 10 that may effectively softly assign responsibility for a given output (e.g., medical report) word to input (e.g., conversation transcript) words (e.g. attention weights, integrated gradient, etc.) according to the model. As a result, this may provide a soft mapping from the transcript word positions to report word positions. In some implementations, the input word position assigned maximal attribution for a given output word may be interpreted as being aligned (linked) to that output (e.g., when a hard mapping is required). Based on the ASR time alignment, a word in the draft medical report, aligned to a word in the ASR conversation transcript, may now be associated with an audio time interval of the associated audio signal of the audio encounter information.

In some implementations, ACD process 10 may also may link (i.e., align) the ASR conversation transcript words with the draft medical report words. For transcript words that may have maximal attribution value for some set of medical report words, ACD process 10 may link them with the first word in that set. For the remaining transcript words, ACD process 10 may link them to the same word that the nearest preceding (or if none, nearest subsequent) conversation transcript word is linked to.

In some implementations, a visual recording (e.g., video stream of the patient encounter), if available, may also be a layer and may be time indexed and thus a given point in the recording may be associated with the same time in the audio recording and thus a conversation transcript word and draft report word. In some implementations, if discrete, standardized, actionable data is produced as a second (parallel) output sequence of the sequence to sequence model, then a similar model output attribution technique may be used to align tokens in this actionable data with the ASR conversation transcript words, and thus the audio intervals.

In some implementations, ACD process 10 may generate 304 a user interface displaying a plurality of layers associated with the audio encounter information obtained from at least the first encounter participant. For example, and referring again at least to the example implementation of FIG. 5, an example user interface (e.g., user interface 500) is shown. It will be appreciated that UI 500 is shown merely for example purposes only, and that more or less features and arrangements of features may be used without departing from the scope of the present disclosure.

As can be seen from FIG. 5, UI 500 includes the first layer of the plurality of layers (e.g., first layer 502 which may be a visualization and/or direct play-back of an audio signal associated with the audio encounter information (e.g., complete audio of the encounter, encompassing and clearly delineating each participant), second layer 504 of the plurality of layers which may be a transcript (e.g., encounter transcript 234) associated with the audio encounter information (e.g., a diarized audio transcript (verbatim) for each participant in the encounter), and third layer 506 of the plurality of layers which may be a medical report (e.g., medical report/record 236) associated with the audio encounter information (e.g., a draft medical report in the appropriate clinical output format). It will be appreciated that that each layer (audio, transcript, draft report, etc.) may be rendered in multiple different ways, and in the most appropriate way for a given use/preference of the end-user.

As such, the specific rendering of layers should be taken as example only and not to limit the scope of the disclosure.

As noted above, encounter transcript 234 (via second layer 504) and/or medical record/record 236 (via third layer 506) may be reviewed by a medical professional involved with the patient encounter (e.g., a visit to a doctor's office) to determine the accuracy of the same and/or make corrections to the same. For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

As such, and referring again at least to the example implementation of FIG. 6, assume for example purposes only that a scribe is reviewing the encounter information using UI 500. In some implementations, ACD process 10 may receive a selection of a first portion of the audio encounter information at a first layer of the plurality of layers on the user interface, and ACD process 10 may display an annotation of at least one of a second layer of the plurality of layers and a third layer of the plurality of layers corresponding to the first portion of the audio encounter information of the first layer of the plurality of layers selected on the user interface. For instance, the scribe may use, e.g., cursor 508 or other known input techniques, to select a portion of first layer 502 (i.e., the audio information of the audio encounter information), which may be received by ACD process 10. As a result, in some implementations, ACD process 10 may display some kind of annotation of either the second layer (e.g., the portion of the transcript associated with the selected portion of the first layer) and/or the third layer (e.g., the portion of the medical report associated with the selected portion of the first layer). In the example, ACD process 10 has displayed an annotation (e.g., bold font) of the second layer (e.g., the portion of the transcript associated with the selected portion of the first layer) and the third layer (e.g., the portion of the medical report associated with the selected portion of the first layer). It will be appreciated that any type of annotation may be used (e.g., bold, italics, underline, highlights, shading, transparency, etc.) without departing from the scope of the present disclosure. As such, the use of bolding as the annotation should be taken as example only and not to otherwise limit the scope of the disclosure.

Similarly, in some implantations, ACD process 10 may receive a selection of the first portion of the audio encounter information at one of the second layer of the plurality of layers and the third layer of the plurality of layers on the user interface, and ACD process 10 may provide audio of the first layer corresponding to the first portion of the audio encounter information of one of the second layer of the plurality of layers and the third layer of the plurality of layers selected on the user interface. For example, and referring to the example implementation of FIG. 7, the scribe may use, e.g., cursor 508 or other known input techniques, to select a portion of second layer 504 (e.g., the transcript), and/or the third layer (e.g., the medical report) which may be received by ACD process 10. As a result, in some implementations, ACD process 10 may provide the audio of first layer 502 (e.g., the audio information of the audio encounter associated with the selected portion of second layer 504).

As such, ACD process 10 may leverage the above-noted defined linkages, such that the encounter recording as captured above may be provided to a human scribe (or physician) in such a fashion, so that they may navigate through each of these layers independently and be always in sync. For instance, if the scribe navigates through first layer 502 (audio) by listening, the part of the transcript that corresponds to that part of the audio may be bolded, highlighted, etc. accordingly, as well as the resulting medical report (and if relevant actionable data) from that information. Additionally/alternatively, if the scribe selects a part of the report, the audio/transcript sections that affected that part of the report may be bolded, highlighted, emphasized, etc. This annotation also may correspond to the audio and report "cursor" (e.g., audio cursor 510) moving, e.g., audio may next play from that position and typing/keyboard-navigation may commence from that position in the report. As a result, since each of the plurality of layers may be synchronized, a scribe (or physician, etc.) may later playback the whole patient encounter, navigate (e.g., "clicking" a mouse cursor of other pointing device at any position) in any portion of any of the layers, make edits, and would know which edit/correction belongs to the other sections (layers). More generally, "clicking" (i.e. resetting the cursor) in one viewed layer may annotate and update the cursor in the linked points/excerpts in the other layers.

As noted above, ACD process 10 may generate 602 an alert (e.g., an audio alert or a visual alert such as a pop-up message, text message, email, etc.) to obtain additional encounter information of the patient encounter. For example, ACD process 10 may be aware of the relevant sections of the above-noted medical report sections when processing the obtained encounter information, as well as explicit data points (such as physical exam findings, lab orders, etc.). In the example, as will be discussed below, ACD process 10 may determine that, e.g., additional information may be needed from the patient, since some of the current encounter information obtained so far may be vague, missing, could not be documented/verified (e.g., neurological section, extremities, etc.), or information which would make the patient encounter more compliant to clinical/administrative guidelines. In some implementations, such as the above example, ACD process 10 may generate 602 an alert (e.g., for the physician) to obtain additional encounter information of the patient encounter to address the encounter information deficiencies.

In some implementations, the alert may be generated 602 and provided to the physician (or other healthcare professional) while the patient is still in the examination room to make it easier to then obtain the additional encounter information; however, the alert may be generated at any time. In some implementations, a virtual assistant (e.g., virtual assistant 238 from FIG. 2) may generate and provide the alert to inform any medical professional (e.g., doctors, nurses, physician's assistants, lab technicians, physical therapists, scribes/transcriptionist, etc.) and/or staff members involved in the patient encounter) to gather the additional encounter information. In some implementations, the alert may be provided during a pre-visit portion of the patient encounter (e.g., patient check in) and/or a post-visit portion of the patient encounter (e.g., check out).

In some implementations, processing 302 the first audio encounter information may include comparing 606 at least one layer of the plurality of layers with at least one data source, which may include at least one of physical exam finding information, lab order information, medical condition checklist information, and compliance information. For example, as discussed above with regard to at least FIG. 2, ACD process 10 may be configured to access one or more data sources 118 (e.g., plurality of individual data sources 120, 122, 124, 126, 128), examples of which may include but are not limited to one or more a medical conditions symptoms data source, a prescriptions compatibility data source, a medical insurance coverage data source, a data source storing past/present physical exam findings of the patient, past/present lab order information for the patient, a medical compliance data source, combination thereof, etc.

Continuing with the above example, assume for example purposes only that the information documented in the medical report section of UI 500 denotes that the physician has conducted a standard physical examination for the patient. In the example, assume that the standard physical examination has nine medical points that should be checked for a standard physical examination (e.g., eyes, throat, reflexes, blood pressure, etc.). Further assume in the example that only eight of the nine medical points that should be checked for a standard physical examination have been completed by the physician. In the example, ACD process 10 may use the patient encounter information (e.g., from the medical report) to determine that a standard physical examination has been conducted with only eight medical points being documented, obtain one of the above-noted data sources that indicates that there are nine medical points that should be checked for a standard physical examination, compare 606 the information in the medical report (e.g., the eight documented medical issues) with one of the obtained data sources that indicates that there are nine medical points that should be checked for a standard physical examination, determine that one of the medical points that should be checked for a standard physical examination has not been documented in the medical report (e.g., blood pressure), and generate an alert for the physician to obtain the missing ninth medical point (e.g., blood pressure). In some implementation, the encounter information in the medical report section that was used (at least in part) to determine that an alert should be generated may be annotated (as discussed above) to help the physician confirm that additional information is indeed needed.

As another example, assume that for example purposes only that the information documented in the medical report section of UI 500 denotes that the physician has conducted a standard physical examination for the patient. In the example, assume that the standard physical examination includes a mandatory blood test. Further assume in the example that the physician has not ordered a blood test. In the example, ACD process 10 may use the patient encounter information (e.g., from the medical report) to determine that a standard physical examination has been conducted without a blood test being documented, obtain one of the above-noted data sources that indicates that a blood test should be included for a standard physical examination, compare 606 the information in the medical report (e.g., showing a lack of blood being drawn or blood test being ordered) with one of the obtained data sources that indicates that a blood test should be included for a standard physical examination, determine that the patient's blood should be drawn and a blood test should be ordered for a standard physical examination that has not been documented in the medical report (e.g., blood pressure), and generate an alert for the physician to obtain the missing information (e.g., blood draw/test).

It will be appreciated that while the above example involves an indication of missing information from a medical examination, other examples of missing (or vague) information may be used without departing from the scope of the present disclosure. For instance, ACD process may similarly generate an alert if the information in the medical report indicates additional information may need to be obtained from the patient encounter to be more compliant with clinical/administrative guidelines. As another example, ACD process may similarly generate an alert if the information in the medical report indicates a particular prescription has not been filled/refilled where one of the above-noted data sources indicates that the particular prescription should be filled/refilled. As another example, ACD process may similarly generate an alert if the information in the medical report indicates symptoms of a particular illness that could be verified by examining some part of the patient that has been examined. As such, the specific disclosure of generating an alert for a missed medical examination point should be taken as example only and not to otherwise limit the scope of the present disclosure.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method comprising:
   obtaining, by a computing device, encounter information of a patient encounter, wherein the encounter information includes audio encounter information obtained from at least a first encounter participant;
   processing the audio encounter information obtained from at least the first encounter participant including generating an encounter transcript and populating at least a portion of a medical report;
   generating a user interface displaying a plurality of layers associated with the audio encounter information obtained from at least the first encounter participant;
   determining a confidence level that a time for applying corrections to at least a portion of one or more of the layers is less than a time for manually typing the at least a portion of the one or more layers;
   exposing the one or more layers when the confidence level is above a threshold;
   determining that at least a portion of the audio encounter information lacks relevance to the medical report including a portion of the audio encounter information that does not attribute significant responsibility for the medical report wherein accumulated attribution of the portion of the audio encounter information toward the medical report is below a threshold; and automatically speeding up at least the portion of the audio encounter information that is determined to lack relevance to the medical report while the audio encounter information is being playback.

2. The computer-implemented method of claim 1 wherein processing the first audio encounter information includes defining linkages between each of the plurality of layers associated with the audio encounter information.

3. The computer-implemented method of claim 1 further including:
receiving a user input of a selection of a first portion of the audio encounter information at the first layer of the plurality of layers on the user interface; and
displaying an annotation of at least one of the second layer of the plurality of layers and the third layer of the plurality of layers corresponding to the first portion of the audio encounter information of the first layer of the plurality of layers selected on the user interface.

4. The computer-implemented method of claim 3 wherein receiving the user input includes:
receiving, via the user input, a selection of the first portion of the audio encounter information at one of the second layer of the plurality of layers and the third layer of the plurality of layers on the user interface; and
providing audio of the first layer corresponding to the first portion of the audio encounter information of one of the second layer of the plurality of layers and the third layer of the plurality of layers selected on the user interface.

5. The computer-implemented method of claim 3 wherein the user input is received from a peripheral device that includes at least one of a keyboard, a pointing device, a foot pedal, and a dial, and wherein the user input from the peripheral device includes at least one of:
a keyboard shortcut when the peripheral device is the keyboard;
a pointing device action when the peripheral device is the pointing device;
raising and lowering of the foot pedal when the peripheral device is the foot pedal; and
at least one of a rotating action, an up action, a down action, a left action, a right action, and a pressing action of the dial when the peripheral device is the dial.

6. The computer-implemented method of claim 5 wherein the user input from the peripheral device causes the user interface to at least one of:
switch between sentences in an output of the medical report;
switch between sections in the output of the medical report;
switch between the medical report and the transcript;
one of providing audio of the audio signal and ceasing audio of the audio signal; and
one of speeding up the audio of the audio signal and slowing down the audio of the audio signal.

7. The computer-implemented method of claim 1 wherein a first layer of the plurality of layers is an audio signal associated with the audio encounter information, wherein a second layer of the plurality of layers is a transcript associated with the audio encounter information, and wherein a third layer of the plurality of layers is a medical report associated with the audio encounter information.

8. A computer program product residing on a non-transitory computer readable medium having a plurality of instructions stored thereon which, when executed by a processor, cause the processor to perform operations comprising:

obtaining, by a computing device, encounter information of a patient encounter, wherein the encounter information includes audio encounter information obtained from at least a first encounter participant;
processing the audio encounter information obtained from at least the first encounter participant including generating an encounter transcript and populating at least a portion of a medical report;
generating a user interface displaying a plurality of layers associated with the audio encounter information obtained from at least the first encounter participant;
determining a confidence level that a time for applying corrections to at least a portion of one or more of the layers is less than a time for manually typing the at least a portion of the one or more layers;
exposing the one or more layers when the confidence level is above a threshold;
determining that at least a portion of the audio encounter information lacks relevance to the medical report including a portion of the audio encounter information that does not attribute significant responsibility for the medical report wherein accumulated attribution of the portion of the audio encounter information toward the medical report is below a threshold; and
automatically speeding up at least the portion of the audio encounter information that is determined to lack relevance to the medical report while the audio encounter information is being playback.

9. The computer program product of claim 8 wherein processing the first audio encounter information includes defining linkages between each of the plurality of layers associated with the audio encounter information.

10. The computer program product of claim 8 further including:
receiving a user input of a selection of a first portion of the audio encounter information at the first layer of the plurality of layers on the user interface; and
displaying an annotation of at least one of the second layer of the plurality of layers and the third layer of the plurality of layers corresponding to the first portion of the audio encounter information of the first layer of the plurality of layers selected on the user interface.

11. The computer program product of claim 10 wherein receiving the user input includes:
receiving, via the user input, a selection of the first portion of the audio encounter information at one of the second layer of the plurality of layers and the third layer of the plurality of layers on the user interface; and
providing audio of the first layer corresponding to the first portion of the audio encounter information of one of the second layer of the plurality of layers and the third layer of the plurality of layers selected on the user interface.

12. The computer program product of claim 10 wherein the user input is received from a peripheral device that includes at least one of a keyboard, a pointing device, a foot pedal, and a dial, and wherein the user input from the peripheral device includes at least one of:
a keyboard shortcut when the peripheral device is the keyboard;
a pointing device action when the peripheral device is the pointing device;
raising and lowering of the foot pedal when the peripheral device is the foot pedal; and
at least one of a rotating action, an up action, a down action, a left action, a right action, and a pressing action of the dial when the peripheral device is the dial.

13. The computer program product of claim 8 wherein a first layer of the plurality of layers is an audio signal associated with the audio encounter information, wherein a second layer of the plurality of layers is a transcript associated with the audio encounter information, and wherein a third layer of the plurality of layers is a medical report associated with the audio encounter information.

14. The computer program product of claim 8 wherein the operations further comprise annotating at least a portion of the audio encounter information determined to lack relevance to the medical report.

15. A computing system including a processor and memory configured to perform operations comprising:
  obtaining, by a computing device, encounter information of a patient encounter, wherein the encounter information includes audio encounter information obtained from at least a first encounter participant;
  processing the audio encounter information obtained from at least the first encounter participant including generating an encounter transcript and populating at least a portion of a medical report;
  generating a user interface displaying a plurality of layers associated with the audio encounter information obtained from at least the first encounter participant;
  determining a confidence level that a time for applying corrections to at least a portion of one or more of the layers is less than a time for manually typing the at least a portion of the one or more layers;
  exposing the one or more layers when the confidence level is above a threshold;
  determining that at least a portion of the audio encounter information lacks relevance to the medical report including a portion of the audio encounter information that does not attribute significant responsibility for the medical report wherein accumulated attribution of the portion of the audio encounter information toward the medical report is below a threshold; and
  automatically speeding up at least the portion of the audio encounter information that is determined to lack relevance to the medical report while the audio encounter information is being playback.

16. The computing system of claim 15 wherein processing the first audio encounter information includes defining linkages between each of the plurality of layers associated with the audio encounter information.

17. The computing system of claim 16 wherein the user input is received from a peripheral device that includes at least one of a keyboard, a pointing device, a foot pedal, and a dial, and wherein the user input from the peripheral device includes at least one of:
  a keyboard shortcut when the peripheral device is the keyboard;
  a pointing device action when the peripheral device is the pointing device;
  raising and lowering of the foot pedal when the peripheral device is the foot pedal; and
  at least one of a rotating action, an up action, a down action, a left action, a right action, and a pressing action of the dial when the peripheral device is the dial.

18. The computing system of claim 17 wherein the user input from the peripheral device causes the user interface to at least one of:
  switch between sentences in an output of the medical report;
  switch between sections in the output of the medical report;
  switch between the medical report and the transcript;
  one of providing audio of the audio signal and ceasing audio of the audio signal; and
  one of speeding up the audio of the audio signal and slowing down the audio of the audio signal.

19. The computing system of claim 15 further including:
  receiving a user input of a selection of a first portion of the audio encounter information at the first layer of the plurality of layers on the user interface and displaying an annotation of at least one of the second layer of the plurality of layers and the third layer of the plurality of layers corresponding to the first portion of the audio encounter information of the first layer of the plurality of layers selected on the user interface; and
  receiving, via the user input, a selection of the first portion of the audio encounter information at one of the second layer of the plurality of layers and the third layer of the plurality of layers on the user interface and providing audio of the first layer corresponding to the first portion of the audio encounter information of one of the second layer of the plurality of layers and the third layer of the plurality of layers selected on the user interface.

20. The computing system of claim 15 wherein a first layer of the plurality of layers is an audio signal associated with the audio encounter information, wherein a second layer of the plurality of layers is a transcript associated with the audio encounter information, and wherein a third layer of the plurality of layers is a medical report associated with the audio encounter information.

* * * * *